United States Patent [19]
Carozzi et al.

[11] Patent Number: 5,686,600
[45] Date of Patent: Nov. 11, 1997

[54] ANTIBODIES WHICH BIND TO INSECT GUT PROTEINS AND THEIR USE

[75] Inventors: Nadine B. Carozzi, Raleigh; Michael G. Koziel, Cary, both of N.C.

[73] Assignee: Novartis Finance Corporation

[21] Appl. No.: 442,542

[22] Filed: May 16, 1995

Related U.S. Application Data

[62] Division of Ser. No. 267,641, Jun. 28, 1994.

[51] Int. Cl.$^6$ .......................... C07H 21/04; C07K 16/00; C07K 16/18; C07K 16/46
[52] U.S. Cl. ................................. 536/23.53; 530/387.3; 530/388.1; 530/387.1
[58] Field of Search ...................... 536/23.53; 530/387.1, 530/388.1, 387.3

[56] References Cited

U.S. PATENT DOCUMENTS

| | | | |
|---|---|---|---|
| 4,816,567 | 3/1989 | Cabilly et al. | 530/387.1 |
| 4,946,778 | 8/1990 | Ladner et al. | 435/69.6 |
| 5,196,320 | 3/1993 | Gillies | 435/697 |
| 5,290,914 | 3/1994 | Wilcox et al. | 530/350 |
| 5,306,628 | 4/1994 | Sivasubramanian et al. | 435/69.7 |

FOREIGN PATENT DOCUMENTS

| | | |
|---|---|---|
| 0438312A2 | 1/1991 | European Pat. Off. . |
| WO91/06320 | 5/1991 | WIPO . |
| WO 91/17254 | 11/1991 | WIPO . |

OTHER PUBLICATIONS

Graf et al. [FEBS Lett 300(2):119–122 (1992)].
Batra, J.K., et al., "single–Chain Immunotoxins Directed at the Human Transferrin Receptor Containing Pseudomonas Exotoxim A or Diptheria Toxin; Anti–TFR(Fv)–PE40 and DT388–Anti–TRF(Fv)", *Molecular and Cellular Biology*, 11(4):2200–2205 (1991).
Brinkmann, U. et al., "B3(Fv)–PE38KDEL, a Single–chain Immunotoxin That Causes Complete Regression of a Human Carcinoma in Mice", *PNAS*, 88:8616–8620 (1991).
Chaudhary, V.K., et al., "A Recombinant Immunotoxin Consisting of Two Antibody Variable Domains Fused to Pseudomonas Exotoxin", *Nature*, 339:394–397 (1989).
Chaudhary, V.K., et al., "A Recombinant Single–chain Immunotoxin Composed of Anti–Tac Variable Regions and a Truncated Diphtheria Toxin", *PNAS*, 87:9491–9494 (1990).
Oddou, P., et al., "Identification and characterization of *Heliothis virescens* midgut membrane proteins binding *Bacillus thuringiensis* δ–endotoxins", *Eur. J. Biochem.*, 202:673–680 (1991).
Oddou, P., et al., "Immunologically unrelated Heliothis sp. and Spodoptera sp. midgut membrane–proteins bind *Bacillus thuringiensis* CryIA(b) δ–endotoxin", *Eur. J. Biochem.*, 212:145–150 (1993).
Pastan, I. et al., "Recombinant Toxins as Novel Therapeutic Agents", *Annu. Rev. Biochem.*, 61:331–354 (1992).
Federici, B.A., "Insecticidal Bacterial Proteins Identify the Midgut Epithelium as a Source of Novel Target Sites for Insect Control", *Archives of Insect Biochemistry and Physiology*, 22;357–371 (1993).
Azuma et al., "Discrete Localization of Distinct Alkaline Phosphatase Isozymes in the Cell Surface of Silkworm Midgut Epithelium", *The Journal of Experimental Zoology*, 251:108–112 (1989).
Crankshaw et al., "Interspecies Cross–Reactivity of an Antibody to Southern Armyworm (*Spodoptera eridania*) Midgut Nadphcytochrome C Reductase", *Insect. Biochem.*, 11(5):593–597 (1981).
Gutierrez et al., "Antibodies from Chagas Patients Serum Bind to the Gut Epithelial Cell Surface of *Triatoma infestans*", *Micr. Electr. Biol. Cel.*, 15(2):145–158 (1991).
Hiatt et al., "Monoclonal antibody engineering in plants", *FEBS*, 307(1):71–75 (1992).
Ryerse et al., "Peritrophic Membrane Structure and Formation in the Larva of a Moth, Heliothis", *Tissue and Cell*, 24(5):751–771 (1992).
Schots et al., "Plantibodies': a flexible approach to design resistance against pathogens", *Neth. J. Pl. Path.*, 98(2):183–191 (1992).
Tavladoraki et al., "Transgenic plants expressing a functional single–chain Fv antibody are specifically protected from virus attack", *Nature*, 366:469–472 (1993).

*Primary Examiner*—Frank C. Eisenschenk
*Attorney, Agent, or Firm*—Gary M. Pace

[57] ABSTRACT

Antibodies, monoclonal antibodies or fragments thereof which bind to brush border membrane vesicles of insect gut and the gene or genes which encode these proteins are provided. The monoclonal antibodies bind the gut of a target insect but do not bind to mammalian brush border membranes or to plant microsomes. The antibodies and the genes encoding them find use in constructing hybrid toxins for control of insect pests.

6 Claims, 1 Drawing Sheet

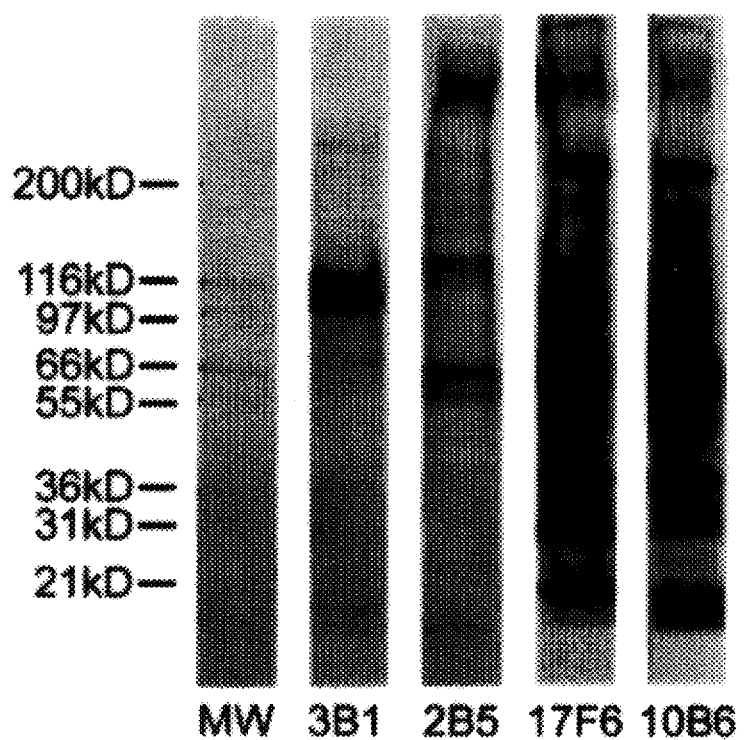

SEQUENCE LISTING ( 1 ) GENERAL INFORMATION:

( i i i ) NUMBER OF SEQUENCES: 49

( 2 ) INFORMATION FOR SEQ ID NO:1:

( i ) SEQUENCE CHARACTERISTICS:
        ( A ) LENGTH: 357 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..357
        ( D ) OTHER INFORMATION: /note="3B1 heavy chain variable region from pCIB4613"

(x i) SEQUENCE DESCRIPTION: SEQ ID NO:1:

| CAG | GTC | AAA | CTG | CAG | GAG | TCT | GGT | GGA | GGA | TTG | GTG | CAG | CCT | AAA | GGG | 48 |
| Gln | Val | Lys | Leu | Gln | Glu | Ser | Gly | Gly | Gly | Leu | Val | Gln | Pro | Lys | Gly | |
| 1 | | | | 5 | | | | | 10 | | | | | 15 | | |

| TCA | TTG | AAA | CTC | TCA | TGT | GCA | GCC | TCT | GGA | TTC | ACC | TTC | AAT | AAC | TTC | 96 |
| Ser | Leu | Lys | Leu | Ser | Cys | Ala | Ala | Ser | Gly | Phe | Thr | Phe | Asn | Asn | Phe | |
| | 20 | | | | 25 | | | | | 30 | | | | | | |

| GCC | ATG | AAC | TGG | GTC | CGC | CAG | GCT | CCA | GGA | AAG | GGT | TTG | GAA | TGG | GTT | 144 |
| Ala | Met | Asn | Trp | Val | Arg | Gln | Ala | Pro | Gly | Lys | Gly | Leu | Glu | Trp | Val | |
| 35 | | | | 40 | | | | | 45 | | | | | | | |

| GCT | CGC | ATA | AGA | AGT | AAA | AGT | AAT | AAT | TAT | GCA | ACA | TCT | TAT | GGC | GAT | 192 |
| Ala | Arg | Ile | Arg | Ser | Lys | Ser | Asn | Asn | Tyr | Ala | Thr | Ser | Tyr | Gly | Asp | |
| | 50 | | | | 55 | | | | | 60 | | | | | | |

| TCA | GTG | AAA | GAC | AGG | TTC | ACC | GTC | TCC | AGA | GAT | GAT | TCA | CAA | AGC | ATG | 240 |
| Ser | Val | Lys | Asp | Arg | Phe | Thr | Val | Ser | Arg | Asp | Asp | Ser | Gln | Ser | Met | |
| 65 | | | | | 70 | | | | | 75 | | | | | 80 | |

| TTC | TAT | CTG | CAA | ATG | AAC | AAC | TTG | AAA | ACT | GAG | GAC | ACA | GCC | ATG | TAT | 288 |
| Phe | Tyr | Leu | Gln | Met | Asn | Asn | Leu | Lys | Thr | Glu | Asp | Thr | Ala | Met | Tyr | |
| 85 | | | | | 90 | | | | | 95 | | | | | | |

| TAC | TGT | GTG | AGG | GTA | GTA | TAC | GGT | GCT | ATG | GAC | TAC | TGG | GGT | CAA | GGA | 336 |
| Tyr | Cys | Val | Arg | Val | Val | Tyr | Gly | Ala | Met | Asp | Tyr | Trp | Gly | Gln | Gly | |
| | 100 | | | | 105 | | | | | 110 | | | | | | |

| ACC | TCA | GTC | ACC | GTC | TCC | TCA | | | | | | | | | | 357 |
| Thr | Ser | Val | Thr | Val | Ser | Ser | | | | | | | | | | |
| 115 | | | | | | | | | | | | | | | | |

(2) INFORMATION FOR SEQ ID NO:2:

(i) SEQUENCE CHARACTERISTICS:
(A) LENGTH: 119 amino acids
(B) TYPE: amino acid
(D) TOPOLOGY: linear (ii) MOLECULE TYPE: protein (x i) SEQUENCE DESCRIPTION: SEQ ID NO:2:

| Gln | Val | Lys | Leu | Gln | Glu | Ser | Gly | Gly | Gly | Leu | Val | Gln | Pro | Lys | Gly |
| 1 | | | | 5 | | | | | 10 | | | | | 15 | |

| Ser | Leu | Lys | Leu | Ser | Cys | Ala | Ala | Ser | Gly | Phe | Thr | Phe | Asn | Asn | Phe |
| | 20 | | | | 25 | | | | | 30 | | | | | |

| Ala | Met | Asn | Trp | Val | Arg | Gln | Ala | Pro | Gly | Lys | Gly | Leu | Glu | Trp | Val |
| 35 | | | | 40 | | | | | 45 | | | | | | |

| Ala | Arg | Ile | Arg | Ser | Lys | Ser | Asn | Asn | Tyr | Ala | Thr | Ser | Tyr | Gly | Asp |
| | 50 | | | | 55 | | | | | 60 | | | | | |

| Ser | Val | Lys | Asp | Arg | Phe | Thr | Val | Ser | Arg | Asp | Asp | Ser | Gln | Ser | Met |
| 65 | | | | | 70 | | | | | 75 | | | | | 80 |

| Phe | Tyr | Leu | Gln | Met | Asn | Asn | Leu | Lys | Thr | Glu | Asp | Thr | Ala | Met | Tyr |
| 85 | | | | | 90 | | | | | 95 | | | | | |

| Tyr | Cys | Val | Arg | Val | Val | Tyr | Gly | Ala | Met | Asp | Tyr | Trp | Gly | Gln | Gly |
| | 100 | | | | 105 | | | | | 110 | | | | | |

| Thr | Ser | Val | Thr | Val | Ser | Ser |
| 115 | | | | | | |

(2) INFORMATION FOR SEQ ID NO:3:

(i) SEQUENCE CHARACTERISTICS:
(A) LENGTH: 333 base pairs
(B) TYPE: nucleic acid
(C) STRANDEDNESS: single
(D) TOPOLOGY: linear ( i i ) MOLECULE TYPE: cDNA ( i x ) FEATURE:
    ( A ) NAME/KEY: CDS
    ( B ) LOCATION: 1..333
    ( D ) OTHER INFORMATION: /note="3B1 light chain variable
        region from pCIB4614 (#21Fv Ab)"

( x i ) SEQUENCE DESCRIPTION: SEQ ID NO:3:

```
GAC ATT GTG CTG ACC CAG TCT CCA GCT TCT TTG GCT GTG TCT CTA GGG      48
Asp Ile Val Leu Thr Gln Ser Pro Ala Ser Leu Ala Val Ser Leu Gly
 1               5                  10                  15

CAG AGG GCC ACC ATC TCC TGC AGA GCC AGC GAA AGT GTT GAT CAT TAT      96
Gln Arg Ala Thr Ile Ser Cys Arg Ala Ser Glu Ser Val Asp His Tyr
         20                  25                  30

GAC ATT AGT TTT ATG AAC TGG TTC CAA CAG AAA CCA GGA CAG CCA CCC     144
Asp Ile Ser Phe Met Asn Trp Phe Gln Gln Lys Pro Gly Gln Pro Pro
 35                  40                  45

AAA CTC CTC ATC TAT GCT GCA TCC AAC CAA GGA TCC GGG GTC CCT GCC     192
Lys Leu Leu Ile Tyr Ala Ala Ser Asn Gln Gly Ser Gly Val Pro Ala
         50                  55                  60

AGG TTT AGT GGC AGT GGG TCT GGG ACA GAC TTC AGC CTC AAC ATC CAT     240
Arg Phe Ser Gly Ser Gly Ser Gly Thr Asp Phe Ser Leu Asn Ile His
 65                  70                  75                  80

CCT ATG GAG GAG GAT GAT ACT GCA ATA TAT TTC TGT CAG CAA AGT AGG     288
Pro Met Glu Glu Asp Asp Thr Ala Ile Tyr Phe Cys Gln Gln Ser Arg
         85                  90                  95

GAA CTT CCG TAC ACG TTC GGA GGG GGG ACC ACG CTG GAA ATA AAA         333
Glu Leu Pro Tyr Thr Phe Gly Gly Gly Thr Thr Leu Glu Ile Lys
        100                 105                 110
```

( 2 ) INFORMATION FOR SEQ ID NO:4:

( i ) SEQUENCE CHARACTERISTICS:
        ( A ) LENGTH: 111 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Asp Ile Val Leu Thr Gln Ser Pro Ala Ser Leu Ala Val Ser Leu Gly
 1               5                  10                  15

Gln Arg Ala Thr Ile Ser Cys Arg Ala Ser Glu Ser Val Asp His Tyr
         20                  25                  30

Asp Ile Ser Phe Met Asn Trp Phe Gln Gln Lys Pro Gly Gln Pro Pro
 35                  40                  45

Lys Leu Leu Ile Tyr Ala Ala Ser Asn Gln Gly Ser Gly Val Pro Ala
         50                  55                  60

Arg Phe Ser Gly Ser Gly Ser Gly Thr Asp Phe Ser Leu Asn Ile His
 65                  70                  75                  80

Pro Met Glu Glu Asp Asp Thr Ala Ile Tyr Phe Cys Gln Gln Ser Arg
         85                  90                  95

Glu Leu Pro Tyr Thr Phe Gly Gly Gly Thr Thr Leu Glu Ile Lys
        100                 105                 110
```

( 2 ) INFORMATION FOR SEQ ID NO:5:

( i ) SEQUENCE CHARACTERISTICS:
        ( A ) LENGTH: 372 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
 ( A ) NAME/KEY: CDS
 ( B ) LOCATION: 1..372
 ( D ) OTHER INFORMATION: /note="2B5 heavy chain variable region from pCIB4615"

( x i ) SEQUENCE DESCRIPTION: SEQ ID NO:5:

| CAG | GTG | CAA | CTG | CAG | GAG | TCT | GGA | GGA | GGC | TTG | GTA | CAG | CCT | GGG | GGT | 48 |
|---|---|---|---|---|---|---|---|---|---|---|---|---|---|---|---|---|
| Gln | Val | Gln | Leu | Gln | Glu | Ser | Gly | Gly | Gly | Leu | Val | Gln | Pro | Gly | Gly | |
| 1 | | | | 5 | | | | | 10 | | | | | 15 | | |

| TCT | CTG | AGA | CTC | TCC | TGT | GCA | ACT | TCT | GGG | TTC | ACC | TTC | ACT | GAT | TAC | 96 |
|---|---|---|---|---|---|---|---|---|---|---|---|---|---|---|---|---|
| Ser | Leu | Arg | Leu | Ser | Cys | Ala | Thr | Ser | Gly | Phe | Thr | Phe | Thr | Asp | Tyr | |
| | 20 | | | | | 25 | | | | | 30 | | | | | |

| TAT | ATG | ACC | TGG | GTC | CGC | CAG | CCT | CCA | GGA | AAG | GCA | CTT | GAG | TGG | TTG | 144 |
|---|---|---|---|---|---|---|---|---|---|---|---|---|---|---|---|---|
| Tyr | Met | Thr | Trp | Val | Arg | Gln | Pro | Pro | Gly | Lys | Ala | Leu | Glu | Trp | Leu | |
| 35 | | | | | 40 | | | | | 45 | | | | | | |

| GGT | TTT | ATT | AGA | CAC | AAA | GCT | AAT | GGT | TAC | ACA | ACA | GAA | TAC | AGT | GCA | 192 |
|---|---|---|---|---|---|---|---|---|---|---|---|---|---|---|---|---|
| Gly | Phe | Ile | Arg | His | Lys | Ala | Asn | Gly | Tyr | Thr | Thr | Glu | Tyr | Ser | Ala | |
| | 50 | | | | | 55 | | | | | 60 | | | | | |

| TCT | GTG | AAG | GGT | CGG | TTC | ACC | ATC | TCC | AGA | GAT | AAT | TCC | CAA | AAC | ATC | 240 |
|---|---|---|---|---|---|---|---|---|---|---|---|---|---|---|---|---|
| Ser | Val | Lys | Gly | Arg | Phe | Thr | Ile | Ser | Arg | Asp | Asn | Ser | Gln | Asn | Ile | |
| 65 | | | | | 70 | | | | | 75 | | | | | 80 | |

| CTC | TAT | CTT | CAA | ATG | AAC | ACC | CTG | AGA | GCT | GAG | GAC | AGT | GCC | ACT | TAT | 288 |
|---|---|---|---|---|---|---|---|---|---|---|---|---|---|---|---|---|
| Leu | Tyr | Leu | Gln | Met | Asn | Thr | Leu | Arg | Ala | Glu | Asp | Ser | Ala | Thr | Tyr | |
| 85 | | | | | 90 | | | | | 95 | | | | | | |

| TAC | TGT | GCA | AGA | GAT | ATA | TGC | TAT | GGT | TAC | GAC | GTT | GGG | GCT | CTG | GAC | 336 |
|---|---|---|---|---|---|---|---|---|---|---|---|---|---|---|---|---|
| Tyr | Cys | Ala | Arg | Asp | Ile | Cys | Tyr | Gly | Tyr | Asp | Val | Gly | Ala | Leu | Asp | |
| | 100 | | | | | 105 | | | | | 110 | | | | | |

| TAC | TGG | GGT | CAA | GGA | ACC | TCA | GTC | ACC | GTC | TCC | TCA | | | | | 372 |
|---|---|---|---|---|---|---|---|---|---|---|---|---|---|---|---|---|
| Tyr | Trp | Gly | Gln | Gly | Thr | Ser | Val | Thr | Val | Ser | Ser | | | | | |
| 115 | | | | | 120 | | | | | | | | | | | |

( 2 ) INFORMATION FOR SEQ ID NO:6:

( i ) SEQUENCE CHARACTERISTICS:
 ( A ) LENGTH: 124 amino acids
 ( B ) TYPE: amino acid
 ( D ) TOPOLOGY: linear ( i i ) MOLECULE TYPE: protein ( x i ) SEQUENCE DESCRIPTION: SEQ ID NO:6:

| Gln | Val | Gln | Leu | Gln | Glu | Ser | Gly | Gly | Gly | Leu | Val | Gln | Pro | Gly | Gly |
|---|---|---|---|---|---|---|---|---|---|---|---|---|---|---|---|
| 1 | | | | 5 | | | | | 10 | | | | | 15 | |

| Ser | Leu | Arg | Leu | Ser | Cys | Ala | Thr | Ser | Gly | Phe | Thr | Phe | Thr | Asp | Tyr |
|---|---|---|---|---|---|---|---|---|---|---|---|---|---|---|---|
| | 20 | | | | | 25 | | | | | 30 | | | | |

| Tyr | Met | Thr | Trp | Val | Arg | Gln | Pro | Pro | Gly | Lys | Ala | Leu | Glu | Trp | Leu |
|---|---|---|---|---|---|---|---|---|---|---|---|---|---|---|---|
| 35 | | | | | 40 | | | | | 45 | | | | | |

| Gly | Phe | Ile | Arg | His | Lys | Ala | Asn | Gly | Tyr | Thr | Thr | Glu | Tyr | Ser | Ala |
|---|---|---|---|---|---|---|---|---|---|---|---|---|---|---|---|
| | 50 | | | | | 55 | | | | | 60 | | | | |

| Ser | Val | Lys | Gly | Arg | Phe | Thr | Ile | Ser | Arg | Asp | Asn | Ser | Gln | Asn | Ile |
|---|---|---|---|---|---|---|---|---|---|---|---|---|---|---|---|
| 65 | | | | | 70 | | | | | 75 | | | | | 80 |

| Leu | Tyr | Leu | Gln | Met | Asn | Thr | Leu | Arg | Ala | Glu | Asp | Ser | Ala | Thr | Tyr |
|---|---|---|---|---|---|---|---|---|---|---|---|---|---|---|---|
| 85 | | | | | 90 | | | | | 95 | | | | | |

| Tyr | Cys | Ala | Arg | Asp | Ile | Cys | Tyr | Gly | Tyr | Asp | Val | Gly | Ala | Leu | Asp |
|---|---|---|---|---|---|---|---|---|---|---|---|---|---|---|---|
| | 100 | | | | | 105 | | | | | 110 | | | | |

| Tyr | Trp | Gly | Gln | Gly | Thr | Ser | Val | Thr | Val | Ser | Ser |
|---|---|---|---|---|---|---|---|---|---|---|---|
| 115 | | | | | 120 | | | | | | |

( 2 ) INFORMATION FOR SEQ ID NO:7:

( i ) SEQUENCE CHARACTERISTICS:
        ( A ) LENGTH: 330 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..330
        ( D ) OTHER INFORMATION: /note="2B5 light chain variable
                region from pCIB4616"

( x i ) SEQUENCE DESCRIPTION: SEQ ID NO:7:

```
GAT ATC GTG ATG ACC CAG TCT CCT GCT TCC TTA GCT ATA TCT CTG GGG      48
Asp Ile Val Met Thr Gln Ser Pro Ala Ser Leu Ala Ile Ser Leu Gly
 1               5                  10                  15

CAG AGG GCC ACC ATC TCA TAC AGG GCC AGC AAA AGT GTC AGT ACA TCT      96
Gln Arg Ala Thr Ile Ser Tyr Arg Ala Ser Lys Ser Val Ser Thr Ser
         20                  25                  30

GGC TAT AGT TAT ATG CAC TGG AAC CAA CAG AAA CCA GGA CAG CCA CCC     144
Gly Tyr Ser Tyr Met His Trp Asn Gln Gln Lys Pro Gly Gln Pro Pro
 35                  40                  45

AGA CTC CTC ATC TAT CTT GTA TCC AAC CTA GAA TCT GGG GTC CCT GCC     192
Arg Leu Leu Ile Tyr Leu Val Ser Asn Leu Glu Ser Gly Val Pro Ala
         50                  55                  60

AGG TTC AGT GGC AGT GGG TCT GGG ACA GAC TTC ACC CTC AAC ATC CAT     240
Arg Phe Ser Gly Ser Gly Ser Gly Thr Asp Phe Thr Leu Asn Ile His
 65                  70                  75                  80

CCT GTG GAG GAG GAG GAT GCT GCA ACC TAT TAC TGT CAG CAC ATT AGG     288
Pro Val Glu Glu Glu Asp Ala Ala Thr Tyr Tyr Cys Gln His Ile Arg
         85                  90                  95

GAG CTT ACA CGT TCG GAG GGG GGA CCA AAG CTG GAA ATA AAA              330
Glu Leu Thr Arg Ser Glu Gly Gly Pro Lys Leu Glu Ile Lys
 100                 105                 110
```

( 2 ) INFORMATION FOR SEQ ID NO:8:

( i ) SEQUENCE CHARACTERISTICS:
        ( A ) LENGTH: 110 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Asp Ile Val Met Thr Gln Ser Pro Ala Ser Leu Ala Ile Ser Leu Gly
 1               5                  10                  15

Gln Arg Ala Thr Ile Ser Tyr Arg Ala Ser Lys Ser Val Ser Thr Ser
         20                  25                  30

Gly Tyr Ser Tyr Met His Trp Asn Gln Gln Lys Pro Gly Gln Pro Pro
 35                  40                  45

Arg Leu Leu Ile Tyr Leu Val Ser Asn Leu Glu Ser Gly Val Pro Ala
         50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ile Arg
         85                  90                  95

Glu Leu Thr Arg Ser Glu Gly Gly Pro Lys Leu Glu Ile Lys
 100                 105                 110
```

( 2 ) INFORMATION FOR SEQ ID NO:9:

( i ) SEQUENCE CHARACTERISTICS:
        ( A ) LENGTH: 165 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..165
        ( D ) OTHER INFORMATION: /note="17F6 heavy chain variable
            region"

( x i ) SEQUENCE DESCRIPTION: SEQ ID NO:9:

```
TCT  GTG  AAA  GGC  AGA  TTC  ACT  ATT  TCA  AGA  GAT  GAT  TCA  CAA  AGT  ACT      48
Ser  Val  Lys  Gly  Arg  Phe  Thr  Ile  Ser  Arg  Asp  Asp  Ser  Gln  Ser  Thr
 1              5                        10                       15

GTC  TAC  CTG  GAG  ATG  AAC  ACG  CTA  AGA  GAG  GAA  GAC  ACT  GCC  ACT  TAT      96
Val  Tyr  Leu  Glu  Met  Asn  Thr  Leu  Arg  Glu  Glu  Asp  Thr  Ala  Thr  Tyr
          20                       25                       30

TAT  TGT  TGT  AGA  GGG  GGG  GAG  GAG  GGG  TTT  CCT  TAC  TGG  GGG  CAA  GGG     144
Tyr  Cys  Cys  Arg  Gly  Gly  Glu  Glu  Gly  Phe  Pro  Tyr  Trp  Gly  Gln  Gly
 35                      40                       45

ACT  CTG  GTC  ACT  GTC  TCT  GCA                                                  165
Thr  Leu  Val  Thr  Val  Ser  Ala
          50                  55
```

( 2 ) INFORMATION FOR SEQ ID NO:10:

( i ) SEQUENCE CHARACTERISTICS:
        ( A ) LENGTH: 55 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

```
Ser  Val  Lys  Gly  Arg  Phe  Thr  Ile  Ser  Arg  Asp  Asp  Ser  Gln  Ser  Thr
 1              5                        10                       15

Val  Tyr  Leu  Glu  Met  Asn  Thr  Leu  Arg  Glu  Glu  Asp  Thr  Ala  Thr  Tyr
          20                       25                       30

Tyr  Cys  Cys  Arg  Gly  Gly  Glu  Glu  Gly  Phe  Pro  Tyr  Trp  Gly  Gln  Gly
 35                      40                       45

Thr  Leu  Val  Thr  Val  Ser  Ala
          50                  55
```

( 2 ) INFORMATION FOR SEQ ID NO:11:

( i ) SEQUENCE CHARACTERISTICS:
        ( A ) LENGTH: 339 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..339
        ( D ) OTHER INFORMATION: /note="17F6 light chain variable
            region"

( x i ) SEQUENCE DESCRIPTION: SEQ ID NO:11:

```
GAC  ATC  GTG  CTG  ACC  CAA  TCT  CCA  TCC  TCC  CTG  AGT  GTG  TCA  GTA  GGA      48
Asp  Ile  Val  Leu  Thr  Gln  Ser  Pro  Ser  Ser  Leu  Ser  Val  Ser  Val  Gly
 1              5                        10                       15
```

```
GAG  AAG  GTC  ACC  ATG  AGC  TGC  AAG  TCC  AGT  CAG  AGT  CTT  TTC  GAC  AGT         96
Glu  Lys  Val  Thr  Met  Ser  Cys  Lys  Ser  Ser  Gln  Ser  Leu  Phe  Asp  Ser
     20                  25                       30

GGA  AAT  CAA  AAG  AAC  TCC  TTG  GCC  TGG  TAT  CAG  CAG  AAA  CCA  GGG  CAG        144
Gly  Asn  Gln  Lys  Asn  Ser  Leu  Ala  Trp  Tyr  Gln  Gln  Lys  Pro  Gly  Gln
 35                       40                       45

CCT  CCT  AAA  CTA  TTG  ATC  TAC  GGG  ACA  TCC  ACT  AGG  GAT  TCT  GGG  GTC        192
Pro  Pro  Lys  Leu  Leu  Ile  Tyr  Gly  Thr  Ser  Thr  Arg  Asp  Ser  Gly  Val
      50                       55                       60

CCT  GAT  CGC  TTC  ACA  GGC  AGT  GGA  TCT  GGG  ACC  GAT  TTC  ACT  CTT  ACC        240
Pro  Asp  Arg  Phe  Thr  Gly  Ser  Gly  Ser  Gly  Thr  Asp  Phe  Thr  Leu  Thr
 65                       70                       75                       80

ATC  AGT  GGT  ATA  CAG  GCT  GAA  GAC  CTG  GCA  GTT  TAT  TAC  TGT  CAG  AAT        288
Ile  Ser  Gly  Ile  Gln  Ala  Glu  Asp  Leu  Ala  Val  Tyr  Tyr  Cys  Gln  Asn
 85                       90                       95

GAT  CAT  TAT  TAT  CCG  TTC  ACG  TTC  GGA  GGG  GGG  ACC  AAG  CTG  GAG  ATA        336
Asp  His  Tyr  Tyr  Pro  Phe  Thr  Phe  Gly  Gly  Gly  Thr  Lys  Leu  Glu  Ile
     100                      105                      110

AAA                                                                                    339
Lys
```

( 2 ) INFORMATION FOR SEQ ID NO:12:

( i ) SEQUENCE CHARACTERISTICS:
        ( A ) LENGTH: 113 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

```
Asp  Ile  Val  Leu  Thr  Gln  Ser  Pro  Ser  Ser  Leu  Ser  Val  Ser  Val  Gly
 1                    5                      10                      15

Glu  Lys  Val  Thr  Met  Ser  Cys  Lys  Ser  Ser  Gln  Ser  Leu  Phe  Asp  Ser
     20                  25                       30

Gly  Asn  Gln  Lys  Asn  Ser  Leu  Ala  Trp  Tyr  Gln  Gln  Lys  Pro  Gly  Gln
 35                       40                       45

Pro  Pro  Lys  Leu  Leu  Ile  Tyr  Gly  Thr  Ser  Thr  Arg  Asp  Ser  Gly  Val
      50                       55                       60

Pro  Asp  Arg  Phe  Thr  Gly  Ser  Gly  Ser  Gly  Thr  Asp  Phe  Thr  Leu  Thr
 65                       70                       75                       80

Ile  Ser  Gly  Ile  Gln  Ala  Glu  Asp  Leu  Ala  Val  Tyr  Tyr  Cys  Gln  Asn
 85                       90                       95

Asp  His  Tyr  Tyr  Pro  Phe  Thr  Phe  Gly  Gly  Gly  Thr  Lys  Leu  Glu  Ile
     100                      105                      110

Lys
```

( 2 ) INFORMATION FOR SEQ ID NO:13:

( i ) SEQUENCE CHARACTERISTICS:
        ( A ) LENGTH: 357 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( i x ) FEATURE:
        ( A ) NAME/KEY: CDS ( B ) LOCATION: 1..357
( D ) OTHER INFORMATION: /note="10B6 heavy chain variable region"

( x i ) SEQUENCE DESCRIPTION: SEQ ID NO:13:

| GAG | GTG | AAG | GTG | GAT | GAG | AGT | GGG | GGA | GGC | TTG | GTG | AGG | CCT | GGA | AAT | 48 |
| Glu | Val | Lys | Val | Asp | Glu | Ser | Gly | Gly | Gly | Leu | Val | Arg | Pro | Gly | Asn | |
| 1 | | | | 5 | | | | | 10 | | | | | 15 | | |

| TCT | CTG | AAA | CTC | TCC | TGT | GAA | ACC | TCG | GGA | TTC | ACT | TTC | AGT | TAT | TAT | 96 |
| Ser | Leu | Lys | Leu | Ser | Cys | Glu | Thr | Ser | Gly | Phe | Thr | Phe | Ser | Tyr | Tyr | |
| | 20 | | | | | 25 | | | | | 30 | | | | | |

| TGG | ATG | CAC | TGG | CTT | CGC | CAG | CCT | CCA | GGG | AAG | AGG | CTG | GAG | TGG | ATT | 144 |
| Trp | Met | His | Trp | Leu | Arg | Gln | Pro | Pro | Gly | Lys | Arg | Leu | Glu | Trp | Ile | |
| 35 | | | | | 40 | | | | | 45 | | | | | | |

| GCT | GTG | ATT | AAA | GTC | AAA | TCT | GCT | AAT | TAT | GGA | TCA | AAT | TAT | GCA | GAG | 192 |
| Ala | Val | Ile | Lys | Val | Lys | Ser | Ala | Asn | Tyr | Gly | Ser | Asn | Tyr | Ala | Glu | |
| | 50 | | | | | 55 | | | | | 60 | | | | | |

| TCT | GTG | AAA | GGC | AGA | TTC | ACT | ATT | TCA | AGA | GAT | GAT | TCA | AAT | AGC | GGT | 240 |
| Ser | Val | Lys | Gly | Arg | Phe | Thr | Ile | Ser | Arg | Asp | Asp | Ser | Asn | Ser | Gly | |
| 65 | | | | | 70 | | | | | 75 | | | | | 80 | |

| GTC | TAC | CTG | CAG | ATG | AAC | AGA | TTA | AGA | GAA | GAA | GAC | ACT | GCC | ACT | TAT | 288 |
| Val | Tyr | Leu | Gln | Met | Asn | Arg | Leu | Arg | Glu | Glu | Asp | Thr | Ala | Thr | Tyr | |
| 85 | | | | | 90 | | | | | 95 | | | | | | |

| TAT | TGT | AGT | AGA | GGG | GGG | GCC | CCC | GGG | TTT | CCT | TAT | TGG | GGC | CAA | GGG | 336 |
| Tyr | Cys | Ser | Arg | Gly | Gly | Ala | Pro | Gly | Phe | Pro | Tyr | Trp | Gly | Gln | Gly | |
| | 100 | | | | | 105 | | | | | | 110 | | | | |

| ACT | CTG | GTC | ACT | GTC | TCT | GCA | | | | | | | | | | 357 |
| Thr | Leu | Val | Thr | Val | Ser | Ala | | | | | | | | | | |
| 115 | | | | | | | | | | | | | | | | |

( 2 ) INFORMATION FOR SEQ ID NO:14:

( i ) SEQUENCE CHARACTERISTICS:
( A ) LENGTH: 119 amino acids
( B ) TYPE: amino acid
( D ) TOPOLOGY: linear ( i i ) MOLECULE TYPE: protein ( x i ) SEQUENCE DESCRIPTION: SEQ ID NO:14:

| Glu | Val | Lys | Val | Asp | Glu | Ser | Gly | Gly | Gly | Leu | Val | Arg | Pro | Gly | Asn |
| 1 | | | | 5 | | | | | 10 | | | | | 15 | |

| Ser | Leu | Lys | Leu | Ser | Cys | Glu | Thr | Ser | Gly | Phe | Thr | Phe | Ser | Tyr | Tyr |
| | 20 | | | | | 25 | | | | | 30 | | | | |

| Trp | Met | His | Trp | Leu | Arg | Gln | Pro | Pro | Gly | Lys | Arg | Leu | Glu | Trp | Ile |
| 35 | | | | | 40 | | | | | 45 | | | | | |

| Ala | Val | Ile | Lys | Val | Lys | Ser | Ala | Asn | Tyr | Gly | Ser | Asn | Tyr | Ala | Glu |
| | 50 | | | | | 55 | | | | | 60 | | | | |

| Ser | Val | Lys | Gly | Arg | Phe | Thr | Ile | Ser | Arg | Asp | Asp | Ser | Asn | Ser | Gly |
| 65 | | | | | 70 | | | | | 75 | | | | | 80 |

| Val | Tyr | Leu | Gln | Met | Asn | Arg | Leu | Arg | Glu | Glu | Asp | Thr | Ala | Thr | Tyr |
| 85 | | | | | 90 | | | | | 95 | | | | | |

| Tyr | Cys | Ser | Arg | Gly | Gly | Ala | Pro | Gly | Phe | Pro | Tyr | Trp | Gly | Gln | Gly |
| | 100 | | | | | 105 | | | | | | 110 | | | |

| Thr | Leu | Val | Thr | Val | Ser | Ala |
| 115 | | | | | | |

( 2 ) INFORMATION FOR SEQ ID NO:15:

( i ) SEQUENCE CHARACTERISTICS:
( A ) LENGTH: 339 base pairs
( B ) TYPE: nucleic acid ( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 1..339
( D ) OTHER INFORMATION: /note="10B6 light chain variable region"

( x i ) SEQUENCE DESCRIPTION: SEQ ID NO:15:

| GAT | ATC | GTG | ATC | ACC | CAG | TCT | CCA | TCC | TCC | CTA | AGT | GTG | TCT | TTA | GGA | 48 |
| Asp | Ile | Val | Ile | Thr | Gln | Ser | Pro | Ser | Ser | Leu | Ser | Val | Ser | Leu | Gly | |
| 1 | | | | 5 | | | | | 10 | | | | | 15 | | |

| GAG | AAG | GTC | ACT | TTG | AGC | TGC | AAG | TCC | AGT | CAG | AGT | CTG | TTT | ACC | GGT | 96 |
| Glu | Lys | Val | Thr | Leu | Ser | Cys | Lys | Ser | Ser | Gln | Ser | Leu | Phe | Thr | Gly | |
| | 20 | | | | | 25 | | | | | 30 | | | | | |

| GGA | GAT | CAA | AAG | AAC | TCC | TTG | GCC | TGG | TAC | CAG | CAG | AAA | GCA | GGG | CAG | 144 |
| Gly | Asp | Gln | Lys | Asn | Ser | Leu | Ala | Trp | Tyr | Gln | Gln | Lys | Ala | Gly | Gln | |
| 35 | | | | | 40 | | | | | 45 | | | | | | |

| CCT | CCT | AGA | CTG | TTG | ATC | TAC | GGG | ACT | TCC | ACT | AGG | GAA | TCT | GGG | GTC | 192 |
| Pro | Pro | Arg | Leu | Leu | Ile | Tyr | Gly | Thr | Ser | Thr | Arg | Glu | Ser | Gly | Val | |
| | 50 | | | | | 55 | | | | | 60 | | | | | |

| CCT | GAT | CGC | TTC | ACA | GGC | AGT | GGA | TCT | GGA | ACC | GAT | TTC | ACT | CTT | GCC | 240 |
| Pro | Asp | Arg | Phe | Thr | Gly | Ser | Gly | Ser | Gly | Thr | Asp | Phe | Thr | Leu | Ala | |
| 65 | | | | | 70 | | | | | 75 | | | | | 80 | |

| ATC | AGC | AGT | GTG | CAG | GCT | GAA | GAC | CTG | GCA | GGT | TAT | TAC | TGT | CAG | AAT | 288 |
| Ile | Ser | Ser | Val | Gln | Ala | Glu | Asp | Leu | Ala | Gly | Tyr | Tyr | Cys | Gln | Asn | |
| 85 | | | | | 90 | | | | | 95 | | | | | | |

| GAT | CAT | AGT | TAT | CCA | TTC | ACG | TTC | GGC | TCG | GGG | ACA | ATG | TTG | GAA | GTA | 336 |
| Asp | His | Ser | Tyr | Pro | Phe | Thr | Phe | Gly | Ser | Gly | Thr | Met | Leu | Glu | Val | |
| | 100 | | | | 105 | | | | | 110 | | | | | | |

| AAA | | | | | | | | | | | | | | | | 339 |
| Lys | | | | | | | | | | | | | | | | |

( 2 ) INFORMATION FOR SEQ ID NO:16:

( i ) SEQUENCE CHARACTERISTICS:
( A ) LENGTH: 113 amino acids
( B ) TYPE: amino acid
( D ) TOPOLOGY: linear ( i i ) MOLECULE TYPE: protein ( x i ) SEQUENCE DESCRIPTION: SEQ ID NO:16:

| Asp | Ile | Val | Ile | Thr | Gln | Ser | Pro | Ser | Ser | Leu | Ser | Val | Ser | Leu | Gly |
| 1 | | | | 5 | | | | | 10 | | | | | 15 | |

| Glu | Lys | Val | Thr | Leu | Ser | Cys | Lys | Ser | Ser | Gln | Ser | Leu | Phe | Thr | Gly |
| | 20 | | | | | 25 | | | | | 30 | | | | |

| Gly | Asp | Gln | Lys | Asn | Ser | Leu | Ala | Trp | Tyr | Gln | Gln | Lys | Ala | Gly | Gln |
| 35 | | | | | 40 | | | | | 45 | | | | | |

| Pro | Pro | Arg | Leu | Leu | Ile | Tyr | Gly | Thr | Ser | Thr | Arg | Glu | Ser | Gly | Val |
| | 50 | | | | | 55 | | | | | 60 | | | | |

| Pro | Asp | Arg | Phe | Thr | Gly | Ser | Gly | Ser | Gly | Thr | Asp | Phe | Thr | Leu | Ala |
| 65 | | | | | 70 | | | | | 75 | | | | | 80 |

| Ile | Ser | Ser | Val | Gln | Ala | Glu | Asp | Leu | Ala | Gly | Tyr | Tyr | Cys | Gln | Asn |
| 85 | | | | | 90 | | | | | 95 | | | | | |

| Asp | His | Ser | Tyr | Pro | Phe | Thr | Phe | Gly | Ser | Gly | Thr | Met | Leu | Glu | Val |
| | 100 | | | | 105 | | | | | 110 | | | | | |

Lys ( 2 ) INFORMATION FOR SEQ ID NO:17:

( i ) SEQUENCE CHARACTERISTICS:
        ( A ) LENGTH: 1797 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 1..1797
        ( D ) OTHER INFORMATION: /note="3B1 single chain antibody from pCIB4631"

( x i ) SEQUENCE DESCRIPTION: SEQ ID NO:17:

```
ATG  GGA  TGG  AGC  TGG  ATC  TTT  CTC  TTC  CTC  CTG  TCA  GGA  GCT  GCA  GGT        48
Met  Gly  Trp  Ser  Trp  Ile  Phe  Leu  Phe  Leu  Leu  Ser  Gly  Ala  Ala  Gly
 1                       5                        10                       15

GTC  CAT  TGC  CTA  CTC  GAG  GAC  ATT  GTG  CTG  ACC  CAG  TCT  CCA  GCT  TCT        96
Val  His  Cys  Leu  Leu  Glu  Asp  Ile  Val  Leu  Thr  Gln  Ser  Pro  Ala  Ser
         20                       25                       30

TTG  GCT  GTG  TCT  CTA  GGG  CAG  AGG  GCC  ACC  ATC  TCC  TGC  AGA  GCC  AGC       144
Leu  Ala  Val  Ser  Leu  Gly  Gln  Arg  Ala  Thr  Ile  Ser  Cys  Arg  Ala  Ser
 35                       40                       45

GAA  AGT  GTT  GAT  CAT  TAT  GAC  ATT  AGT  TTT  ATG  AAC  TGG  TTC  CAA  CAG       192
Glu  Ser  Val  Asp  His  Tyr  Asp  Ile  Ser  Phe  Met  Asn  Trp  Phe  Gln  Gln
         50                       55                       60

AAA  CCA  GGA  CAG  CCA  CCC  AAA  CTC  CTC  ATC  TAT  GCT  GCA  TCC  AAC  CAA       240
Lys  Pro  Gly  Gln  Pro  Pro  Lys  Leu  Leu  Ile  Tyr  Ala  Ala  Ser  Asn  Gln
 65                       70                       75                       80

GGA  TCC  GGG  GTC  CCT  GCC  AGG  TTT  AGT  GGC  AGT  GGG  TCT  GGG  ACA  GAC       288
Gly  Ser  Gly  Val  Pro  Ala  Arg  Phe  Ser  Gly  Ser  Gly  Ser  Gly  Thr  Asp
 85                       90                       95

TTC  AGC  CTC  AAC  ATC  CAT  CCT  ATG  GAG  GAG  GAT  GAT  ACT  GCA  ATA  TAT       336
Phe  Ser  Leu  Asn  Ile  His  Pro  Met  Glu  Glu  Asp  Asp  Thr  Ala  Ile  Tyr
        100                      105                      110

TTC  TGT  CAG  CAA  AGT  AGG  GAA  CTT  CCG  TAC  ACG  TTC  GGA  GGG  GGG  ACC       384
Phe  Cys  Gln  Gln  Ser  Arg  Glu  Leu  Pro  Tyr  Thr  Phe  Gly  Gly  Gly  Thr
115                      120                      125

ACG  CTG  GAA  ATA  AAA  CGG  GCT  GAT  GCT  GCA  CCA  ACT  AGA  TCT  GGT  GGC       432
Thr  Leu  Glu  Ile  Lys  Arg  Ala  Asp  Ala  Ala  Pro  Thr  Arg  Ser  Gly  Gly
        130                      135                      140

GGT  GGC  TCG  GGC  GGT  GGT  GGG  TCG  CTC  GAG  CAG  GTC  AAA  CTG  CAG  GAG       480
Gly  Gly  Ser  Gly  Gly  Gly  Gly  Ser  Leu  Glu  Gln  Val  Lys  Leu  Gln  Glu
145                      150                      155                      160

TCT  GGT  GGA  GGA  TTG  GTG  CAG  CCT  AAA  GGG  TCA  TTG  AAA  CTC  TCA  TGT       528
Ser  Gly  Gly  Gly  Leu  Val  Gln  Pro  Lys  Gly  Ser  Leu  Lys  Leu  Ser  Cys
165                      170                      175

GCA  GCC  TCT  GGA  TTC  ACC  TTC  AAT  AAC  TTC  GCC  ATG  AAC  TGG  GTC  CGC       576
Ala  Ala  Ser  Gly  Phe  Thr  Phe  Asn  Asn  Phe  Ala  Met  Asn  Trp  Val  Arg
        180                      185                      190

CAG  GCT  CCA  GGA  AAG  GGT  TTG  GAA  TGG  GTT  GCT  CGC  ATA  AGA  AGT  AAA       624
Gln  Ala  Pro  Gly  Lys  Gly  Leu  Glu  Trp  Val  Ala  Arg  Ile  Arg  Ser  Lys
195                      200                      205

AGT  AAT  AAT  TAT  GCA  ACA  TCT  TAT  GGC  GAT  TCA  GTG  AAA  GAC  AGG  TTC       672
Ser  Asn  Asn  Tyr  Ala  Thr  Ser  Tyr  Gly  Asp  Ser  Val  Lys  Asp  Arg  Phe
        210                      215                      220

ACC  GTC  TCC  AGA  GAT  GAT  TCA  CAA  AGC  ATG  TTC  TAT  CTG  CAA  ATG  AAC       720
Thr  Val  Ser  Arg  Asp  Asp  Ser  Gln  Ser  Met  Phe  Tyr  Leu  Gln  Met  Asn
225                      230                      235                      240

AAC  TTG  AAA  ACT  GAG  GAC  ACA  GCC  ATG  TAT  TAC  TGT  GTG  AGG  GTA  GTA       768
Asn  Leu  Lys  Thr  Glu  Asp  Thr  Ala  Met  Tyr  Tyr  Cys  Val  Arg  Val  Val
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---  |
| 245 |     |     |     |     | 250 |     |     |     |     | 255 |     |     |     |     |     |      |
| TAC | GGT | GCT | ATG | GAC | TAC | TGG | GGT | CAA | GGA | ACC | TCA | GTC | ACC | GTC | TCC | 816  |
| Tyr | Gly | Ala | Met | Asp | Tyr | Trp | Gly | Gln | Gly | Thr | Ser | Val | Thr | Val | Ser |      |
|     |     | 260 |     |     |     | 265 |     |     |     |     | 270 |     |     |     |     |      |
| TCA | GCC | AAA | ACG | ACA | CCC | CCA | TCT | GTC | TAT | CCA | CTG | GCC | CCT | GGA | TCT | 864  |
| Ser | Ala | Lys | Thr | Thr | Pro | Pro | Ser | Val | Tyr | Pro | Leu | Ala | Pro | Gly | Ser |      |
| 275 |     |     |     |     | 280 |     |     |     |     | 285 |     |     |     |     |     |      |
| AGA | TCT | GCT | GCC | CAA | ACT | AAC | TCC | ATG | GTG | ACC | CTG | GGA | TGC | CTG | GTC | 912  |
| Arg | Ser | Ala | Ala | Gln | Thr | Asn | Ser | Met | Val | Thr | Leu | Gly | Cys | Leu | Val |      |
|     | 290 |     |     |     |     | 295 |     |     |     |     | 300 |     |     |     |     |      |
| AAG | GGC | TAT | TTC | CCT | GAG | CCA | GTG | ACA | GTG | ACC | TGG | AAC | TCT | GGA | TCC | 960  |
| Lys | Gly | Tyr | Phe | Pro | Glu | Pro | Val | Thr | Val | Thr | Trp | Asn | Ser | Gly | Ser |      |
| 305 |     |     |     |     | 310 |     |     |     |     | 315 |     |     |     |     | 320 |      |
| CTG | TCC | AGC | GGT | GTG | CAC | ACC | TTC | CCA | GCT | GTC | CTG | CAG | TCT | GAC | CTC | 1008 |
| Leu | Ser | Ser | Gly | Val | His | Thr | Phe | Pro | Ala | Val | Leu | Gln | Ser | Asp | Leu |      |
| 325 |     |     |     |     | 330 |     |     |     |     | 335 |     |     |     |     |     |      |
| TAC | ACT | CTG | AGC | AGC | TCA | GTG | ACT | GTC | CCC | TCC | AGC | ACC | TGG | CCC | AGC | 1056 |
| Tyr | Thr | Leu | Ser | Ser | Ser | Val | Thr | Val | Pro | Ser | Ser | Thr | Trp | Pro | Ser |      |
|     | 340 |     |     |     |     | 345 |     |     |     |     | 350 |     |     |     |     |      |
| GAG | ACC | GTC | ACC | TGC | AAC | GTT | GCC | CAC | CCG | GCC | AGC | AGC | ACC | AAG | GTG | 1104 |
| Glu | Thr | Val | Thr | Cys | Asn | Val | Ala | His | Pro | Ala | Ser | Ser | Thr | Lys | Val |      |
| 355 |     |     |     |     | 360 |     |     |     |     | 365 |     |     |     |     |     |      |
| GAC | AAG | AAA | ATT | GTG | CCC | AGG | GAT | TGT | GGT | TGT | AAG | CCT | TGC | ATA | TGT | 1152 |
| Asp | Lys | Lys | Ile | Val | Pro | Arg | Asp | Cys | Gly | Cys | Lys | Pro | Cys | Ile | Cys |      |
| 370 |     |     |     |     |     | 375 |     |     |     |     | 380 |     |     |     |     |      |
| ACA | GTC | CCA | GAA | GTA | TCA | TCT | GTC | TTC | ATC | TTC | CCC | CCA | AAG | CCC | AAG | 1200 |
| Thr | Val | Pro | Glu | Val | Ser | Ser | Val | Phe | Ile | Phe | Pro | Pro | Lys | Pro | Lys |      |
| 385 |     |     |     |     | 390 |     |     |     |     | 395 |     |     |     |     | 400 |      |
| GAT | GTG | CTC | ACC | ATT | ACT | CTG | ACT | CCT | AAG | GTC | ACG | TGT | GTT | GTG | GTA | 1248 |
| Asp | Val | Leu | Thr | Ile | Thr | Leu | Thr | Pro | Lys | Val | Thr | Cys | Val | Val | Val |      |
| 405 |     |     |     |     | 410 |     |     |     |     | 415 |     |     |     |     |     |      |
| GAC | ATC | AGC | AAG | GAT | GAT | CCC | GAG | GTC | CAG | TTC | AGC | TGG | TTT | GTA | GAT | 1296 |
| Asp | Ile | Ser | Lys | Asp | Asp | Pro | Glu | Val | Gln | Phe | Ser | Trp | Phe | Val | Asp |      |
|     | 420 |     |     |     |     | 425 |     |     |     |     | 430 |     |     |     |     |      |
| GAT | GTG | GAG | GTG | CAC | ACA | GCT | CAG | ACG | CAA | CCC | CGG | GAG | GAG | CAG | TTC | 1344 |
| Asp | Val | Glu | Val | His | Thr | Ala | Gln | Thr | Gln | Pro | Arg | Glu | Glu | Gln | Phe |      |
| 435 |     |     |     |     | 440 |     |     |     |     | 445 |     |     |     |     |     |      |
| AAC | AGC | ACT | TTC | CGC | TCA | GTC | AGT | GAA | CTT | CCC | ATC | ATG | CAC | CAG | GAC | 1392 |
| Asn | Ser | Thr | Phe | Arg | Ser | Val | Ser | Glu | Leu | Pro | Ile | Met | His | Gln | Asp |      |
|     | 450 |     |     |     |     | 455 |     |     |     |     | 460 |     |     |     |     |      |
| TGG | CTC | AAT | GGC | AAG | GAG | TTC | AAA | TGC | AGG | GTC | AAC | AGT | GCA | GCT | TTC | 1440 |
| Trp | Leu | Asn | Gly | Lys | Glu | Phe | Lys | Cys | Arg | Val | Asn | Ser | Ala | Ala | Phe |      |
| 465 |     |     |     |     | 470 |     |     |     |     | 475 |     |     |     |     | 480 |      |
| CCT | GCC | CCC | ATC | GAG | AAA | ACC | ATC | TCC | AAA | ACC | AAA | GGC | AGA | CCG | AAG | 1488 |
| Pro | Ala | Pro | Ile | Glu | Lys | Thr | Ile | Ser | Lys | Thr | Lys | Gly | Arg | Pro | Lys |      |
| 485 |     |     |     |     | 490 |     |     |     |     | 495 |     |     |     |     |     |      |
| GCT | CCA | CAG | GTG | TAC | ACC | ATT | CCA | CCT | CCC | AAG | GAG | CAG | ATG | GCC | AAG | 1536 |
| Ala | Pro | Gln | Val | Tyr | Thr | Ile | Pro | Pro | Pro | Lys | Glu | Gln | Met | Ala | Lys |      |
|     | 500 |     |     |     |     | 505 |     |     |     |     | 510 |     |     |     |     |      |
| GAT | AAA | GTC | AGT | CTG | ACC | TGC | ATG | ATA | ACA | GAC | TTC | TTC | CCT | GAA | GAC | 1584 |
| Asp | Lys | Val | Ser | Leu | Thr | Cys | Met | Ile | Thr | Asp | Phe | Phe | Pro | Glu | Asp |      |
| 515 |     |     |     |     | 520 |     |     |     |     | 525 |     |     |     |     |     |      |
| ATT | ACT | GTG | GAG | TGG | CAG | TGG | AAT | GGG | CAG | CCA | GCG | GAG | AAC | TAC | AAG | 1632 |
| Ile | Thr | Val | Glu | Trp | Gln | Trp | Asn | Gly | Gln | Pro | Ala | Glu | Asn | Tyr | Lys |      |
|     | 530 |     |     |     |     | 535 |     |     |     |     | 540 |     |     |     |     |      |
| AAC | ACT | CAG | CCC | ATC | ATG | AAC | ACG | AAT | GGC | TCT | TAC | TTC | GTC | TAC | AGC | 1680 |
| Asn | Thr | Gln | Pro | Ile | Met | Asn | Thr | Asn | Gly | Ser | Tyr | Phe | Val | Tyr | Ser |      |
| 545 |     |     |     |     | 550 |     |     |     |     | 555 |     |     |     |     | 560 |      |
| AAG | CTC | AAT | GTG | CAG | AAG | AGC | AAC | TGG | GAG | GCA | GGA | AAT | ACT | TTC | ACC | 1728 |
| Lys | Leu | Asn | Val | Gln | Lys | Ser | Asn | Trp | Glu | Ala | Gly | Asn | Thr | Phe | Thr |      |

```
                     565                            570                            575
TGC  TCT  GTC  TTA  CAT  GAG  GGC  CTG  CAC  AAC  CAC  CAT  ACT  GAG  AAG  AGC       1776
Cys  Ser  Val  Leu  His  Glu  Gly  Leu  His  Asn  His  His  Thr  Glu  Lys  Ser
     580                           585                           590

CTC  TCC  CAC  TCT  CCT  GGT  AAA                                                    1797
Leu  Ser  His  Ser  Pro  Gly  Lys
595
```

( 2 ) INFORMATION FOR SEQ ID NO:18:

( i ) SEQUENCE CHARACTERISTICS:
        ( A ) LENGTH: 599 amino acids
        ( B ) TYPE: amino acid
        ( D ) TOPOLOGY: linear ( i i ) MOLECULE TYPE: protein ( x i ) SEQUENCE DESCRIPTION: SEQ ID NO:18:

```
Met  Gly  Trp  Ser  Trp  Ile  Phe  Leu  Phe  Leu  Leu  Ser  Gly  Ala  Ala  Gly
 1                   5                    10                       15

Val  His  Cys  Leu  Leu  Glu  Asp  Ile  Val  Leu  Thr  Gln  Ser  Pro  Ala  Ser
     20                       25                  30

Leu  Ala  Val  Ser  Leu  Gly  Gln  Arg  Ala  Thr  Ile  Ser  Cys  Arg  Ala  Ser
35                       40                       45

Glu  Ser  Val  Asp  His  Tyr  Asp  Ile  Ser  Phe  Met  Asn  Trp  Phe  Gln  Gln
     50                       55                       60

Lys  Pro  Gly  Gln  Pro  Pro  Lys  Leu  Leu  Ile  Tyr  Ala  Ala  Ser  Asn  Gln
65                       70                       75                            80

Gly  Ser  Gly  Val  Pro  Ala  Arg  Phe  Ser  Gly  Ser  Gly  Ser  Gly  Thr  Asp
85                       90                       95

Phe  Ser  Leu  Asn  Ile  His  Pro  Met  Glu  Glu  Asp  Asp  Thr  Ala  Ile  Tyr
     100                      105                      110

Phe  Cys  Gln  Gln  Ser  Arg  Glu  Leu  Pro  Tyr  Thr  Phe  Gly  Gly  Gly  Thr
115                      120                      125

Thr  Leu  Glu  Ile  Lys  Arg  Ala  Asp  Ala  Ala  Pro  Thr  Arg  Ser  Gly  Gly
     130                      135                      140

Gly  Gly  Ser  Gly  Gly  Gly  Gly  Ser  Leu  Glu  Gln  Val  Lys  Leu  Gln  Glu
145                      150                      155                           160

Ser  Gly  Gly  Gly  Leu  Val  Gln  Pro  Lys  Gly  Ser  Leu  Lys  Leu  Ser  Cys
165                      170                      175

Ala  Ala  Ser  Gly  Phe  Thr  Phe  Asn  Asn  Phe  Ala  Met  Asn  Trp  Val  Arg
     180                      185                      190

Gln  Ala  Pro  Gly  Lys  Gly  Leu  Glu  Trp  Val  Ala  Arg  Ile  Arg  Ser  Lys
195                      200                      205

Ser  Asn  Asn  Tyr  Ala  Thr  Ser  Tyr  Gly  Asp  Ser  Val  Lys  Asp  Arg  Phe
     210                      215                      220

Thr  Val  Ser  Arg  Asp  Asp  Ser  Gln  Ser  Met  Phe  Tyr  Leu  Gln  Met  Asn
225                      230                      235                           240

Asn  Leu  Lys  Thr  Glu  Asp  Thr  Ala  Met  Tyr  Tyr  Cys  Val  Arg  Val  Val
     245                      250                      255

Tyr  Gly  Ala  Met  Asp  Tyr  Trp  Gly  Gln  Gly  Thr  Ser  Val  Thr  Val  Ser
     260                      265                      270

Ser  Ala  Lys  Thr  Thr  Pro  Pro  Ser  Val  Tyr  Pro  Leu  Ala  Pro  Gly  Ser
275                      280                      285

Arg  Ser  Ala  Ala  Gln  Thr  Asn  Ser  Met  Val  Thr  Leu  Gly  Cys  Leu  Val
     290                      295                      300

Lys  Gly  Tyr  Phe  Pro  Glu  Pro  Val  Thr  Val  Thr  Trp  Asn  Ser  Gly  Ser
```

|     |     |     |     |     |     |     |     |     |     |     |     |     |     |     |     |
|-----|-----|-----|-----|-----|-----|-----|-----|-----|-----|-----|-----|-----|-----|-----|-----|
| 305 |     |     |     |     | 310 |     |     |     |     | 315 |     |     |     |     | 320 |
| Leu | Ser | Ser | Gly | Val | His | Thr | Phe | Pro | Ala | Val | Leu | Gln | Ser | Asp | Leu |
| 325 |     |     |     |     | 330 |     |     |     |     | 335 |     |     |     |     |     |
| Tyr | Thr | Leu | Ser | Ser | Ser | Val | Thr | Val | Pro | Ser | Ser | Thr | Trp | Pro | Ser |
|     | 340 |     |     |     |     | 345 |     |     |     |     | 350 |     |     |     |     |
| Glu | Thr | Val | Thr | Cys | Asn | Val | Ala | His | Pro | Ala | Ser | Ser | Thr | Lys | Val |
| 355 |     |     |     |     | 360 |     |     |     |     | 365 |     |     |     |     |     |
| Asp | Lys | Lys | Ile | Val | Pro | Arg | Asp | Cys | Gly | Cys | Lys | Pro | Cys | Ile | Cys |
|     | 370 |     |     |     |     | 375 |     |     |     |     | 380 |     |     |     |     |
| Thr | Val | Pro | Glu | Val | Ser | Ser | Val | Phe | Ile | Phe | Pro | Pro | Lys | Pro | Lys |
| 385 |     |     |     |     | 390 |     |     |     |     | 395 |     |     |     |     | 400 |
| Asp | Val | Leu | Thr | Ile | Thr | Leu | Thr | Pro | Lys | Val | Thr | Cys | Val | Val | Val |
| 405 |     |     |     |     | 410 |     |     |     |     | 415 |     |     |     |     |     |
| Asp | Ile | Ser | Lys | Asp | Asp | Pro | Glu | Val | Gln | Phe | Ser | Trp | Phe | Val | Asp |
|     | 420 |     |     |     |     | 425 |     |     |     |     | 430 |     |     |     |     |
| Asp | Val | Glu | Val | His | Thr | Ala | Gln | Thr | Gln | Pro | Arg | Glu | Glu | Gln | Phe |
| 435 |     |     |     |     | 440 |     |     |     |     | 445 |     |     |     |     |     |
| Asn | Ser | Thr | Phe | Arg | Ser | Val | Ser | Glu | Leu | Pro | Ile | Met | His | Gln | Asp |
|     | 450 |     |     |     |     | 455 |     |     |     |     | 460 |     |     |     |     |
| Trp | Leu | Asn | Gly | Lys | Glu | Phe | Lys | Cys | Arg | Val | Asn | Ser | Ala | Ala | Phe |
| 465 |     |     |     |     | 470 |     |     |     |     | 475 |     |     |     |     | 480 |
| Pro | Ala | Pro | Ile | Glu | Lys | Thr | Ile | Ser | Lys | Thr | Lys | Gly | Arg | Pro | Lys |
| 485 |     |     |     |     | 490 |     |     |     |     | 495 |     |     |     |     |     |
| Ala | Pro | Gln | Val | Tyr | Thr | Ile | Pro | Pro | Pro | Lys | Glu | Gln | Met | Ala | Lys |
|     | 500 |     |     |     |     | 505 |     |     |     |     | 510 |     |     |     |     |
| Asp | Lys | Val | Ser | Leu | Thr | Cys | Met | Ile | Thr | Asp | Phe | Phe | Pro | Glu | Asp |
| 515 |     |     |     |     | 520 |     |     |     |     | 525 |     |     |     |     |     |
| Ile | Thr | Val | Glu | Trp | Gln | Trp | Asn | Gly | Gln | Pro | Ala | Glu | Asn | Tyr | Lys |
|     | 530 |     |     |     |     | 535 |     |     |     |     | 540 |     |     |     |     |
| Asn | Thr | Gln | Pro | Ile | Met | Asn | Thr | Asn | Gly | Ser | Tyr | Phe | Val | Tyr | Ser |
| 545 |     |     |     |     | 550 |     |     |     |     | 555 |     |     |     |     | 560 |
| Lys | Leu | Asn | Val | Gln | Lys | Ser | Asn | Trp | Glu | Ala | Gly | Asn | Thr | Phe | Thr |
| 565 |     |     |     |     | 570 |     |     |     |     | 575 |     |     |     |     |     |
| Cys | Ser | Val | Leu | His | Glu | Gly | Leu | His | Asn | His | His | Thr | Glu | Lys | Ser |
|     | 580 |     |     |     |     | 585 |     |     |     |     | 590 |     |     |     |     |
| Leu | Ser | His | Ser | Pro | Gly | Lys |     |     |     |     |     |     |     |     |     |
| 595 |     |     |     |     |     |     |     |     |     |     |     |     |     |     |     |

( 2 ) INFORMATION FOR SEQ ID NO:19:

( i ) SEQUENCE CHARACTERISTICS:
        ( A ) LENGTH: 101 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: oligonucleotide KE109A28 used to make
            101bp Sty I/Bgl II fragment for pCIB4612

( x i ) SEQUENCE DESCRIPTION: SEQ ID NO:19:

```
CAAGGACGAG TATGAACGAC ATAACAGCTA TACCTGTGAG GCCACTCACA AGACATCAAC     60
TTCACCCATT GTCAAGAGCT TCAACAGGAA TGAGTGTTAG G                         101
```

( 2 ) INFORMATION FOR SEQ ID NO:20:

( i ) SEQUENCE CHARACTERISTICS:
        ( A ) LENGTH: 101 base pairs

```
       ( B ) TYPE: nucleic acid
       ( C ) STRANDEDNESS: single
       ( D ) TOPOLOGY: linear ( i i ) MOLECULE TYPE: other nucleic acid
       ( A ) DESCRIPTION: oligonucleotide KE110A28 used to make
             101bp Sty I/Bgl II fragment for pCIB4612

( x i ) SEQUENCE DESCRIPTION: SEQ ID NO:20:

GATCCCTAAC ACTCATTCCT GTTGAAGCTC TTGACAATGG GTGAAGTTGA TGTCTTGTGA         60

GTGGCCTCAC AGGTATAGCT GTTATGTCGT TCATACTCGT C                            101

( 2 ) INFORMATION FOR SEQ ID NO:21:

( i ) SEQUENCE CHARACTERISTICS:
       ( A ) LENGTH: 72 base pairs
       ( B ) TYPE: nucleic acid
       ( C ) STRANDEDNESS: single
       ( D ) TOPOLOGY: linear ( i i ) MOLECULE TYPE: other nucleic acid
       ( A ) DESCRIPTION: oligonucleotide KE111A28 used to make
             71bp Xho I/Dde I fragment for pCIB4612

( x i ) SEQUENCE DESCRIPTION: SEQ ID NO:21:

TCGAGGGTAC CGAGCTCTAG ATCTGTATCC ATCTTCCCAC CATCCAGTGA GCAGTTAACA         60

TCTGGAGGTG CC                                                            72

( 2 ) INFORMATION FOR SEQ ID NO:22:

( i ) SEQUENCE CHARACTERISTICS:
       ( A ) LENGTH: 71 base pairs
       ( B ) TYPE: nucleic acid
       ( C ) STRANDEDNESS: single
       ( D ) TOPOLOGY: linear ( i i ) MOLECULE TYPE: other nucleic acid
       ( A ) DESCRIPTION: oligonucleotide KE112A28 used to make
             71bp Xho I/Dde I fragment for pCIB4612

( x i ) SEQUENCE DESCRIPTION: SEQ ID NO:22:

TGAGGCACCT CCAGATGTTA ACTGCTCACT GGATGGTGGG AAGATGGATA CAGATCTAGA         60

GCTCGGTACC C                                                             71

( 2 ) INFORMATION FOR SEQ ID NO:23:

( i ) SEQUENCE CHARACTERISTICS:
       ( A ) LENGTH: 41 base pairs
       ( B ) TYPE: nucleic acid
       ( C ) STRANDEDNESS: single
       ( D ) TOPOLOGY: linear ( i i ) MOLECULE TYPE: other nucleic acid
       ( A ) DESCRIPTION: oligonucleotide KE106A28 used to make
             40bp Xho I/Nco I fragment for pCIB4611

( x i ) SEQUENCE DESCRIPTION: SEQ ID NO:23:

TCGAGGGTAC CGAGCTCTAG ATCTGCTGCC CAAACTAACT C                            41

( 2 ) INFORMATION FOR SEQ ID NO:24:

( i ) SEQUENCE CHARACTERISTICS:
       ( A ) LENGTH: 41 base pairs
       ( B ) TYPE: nucleic acid
       ( C ) STRANDEDNESS: single
       ( D ) TOPOLOGY: linear ( i i ) MOLECULE TYPE: other nucleic acid
       ( A ) DESCRIPTION: oligonucleotide KE107A28 used to make
```

40bp Xho I/Nco I fragment for pCIB4611

(x i) SEQUENCE DESCRIPTION: SEQ ID NO:24:

CATGGAGTTA GTTTGGGCAG CAGATCTAGA GCTCGGTACC C        41

(2) INFORMATION FOR SEQ ID NO:25:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (i i) MOLECULE TYPE: other nucleic acid
        (A) DESCRIPTION: oligonucleotide KE108A28 used to make
            40bp Bst XI/Bam HI fragment for pCIB4611

(x i) SEQUENCE DESCRIPTION: SEQ ID NO:25:

CTGGTAAAGG CGGCCGCATC GATTAAGTCG ACCCGCGG        39

(2) INFORMATION FOR SEQ ID NO:26:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (i i) MOLECULE TYPE: other nucleic acid
        (A) DESCRIPTION: oligonucleotide KE105A28 used to make
            40bp Bst XI/Bam HI fragment for pCIB4611

(x i) SEQUENCE DESCRIPTION: SEQ ID NO:26:

GATCCCCGCG GGTCGACTTA ATCGATGCGG CCGCCTTTAC CAGGAGA        47

(2) INFORMATION FOR SEQ ID NO:27:

(i) SEQUENCE CHARACTERISTICS:
        (A) LENGTH: 7 base pairs
        (B) TYPE: nucleic acid
        (C) STRANDEDNESS: single
        (D) TOPOLOGY: linear (i i) MOLECULE TYPE: other nucleic acid
        (A) DESCRIPTION: plant consensus translational initiation
            sequence for pCIB4610

(x i) SEQUENCE DESCRIPTION: SEQ ID NO:27:

AACAATG        7

(2) INFORMATION FOR SEQ ID NO:28:

(i) SEQUENCE CHARACTERISTICS:
        (A) LENGTH: 7 base pairs
        (B) TYPE: nucleic acid
        (C) STRANDEDNESS: single
        (D) TOPOLOGY: linear (i i) MOLECULE TYPE: other nucleic acid
        (A) DESCRIPTION: plant consensus translational initiation
            sequence for pCIB4600

(x i) SEQUENCE DESCRIPTION: SEQ ID NO:28:

TCCGATG        7

(2) INFORMATION FOR SEQ ID NO:29:

(i) SEQUENCE CHARACTERISTICS:
        (A) LENGTH: 25 base pairs
        (B) TYPE: nucleic acid ( C ) STRANDEDNESS: single
( D ) TOPOLOGY: linear ( i i ) MOLECULE TYPE: other nucleic acid
( A ) DESCRIPTION: PCR primer KE102A28 used to generate 83bp fragment for pCIB4610

( x i ) SEQUENCE DESCRIPTION: SEQ ID NO:29:

CGAAGTTAAC AGATCTAGAG CTCGG   25

( 2 ) INFORMATION FOR SEQ ID NO:30:

( i ) SEQUENCE CHARACTERISTICS:
( A ) LENGTH: 32 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: PCR primer KE101A28 used to generate 83bp fragment for pCIB4610

( x i ) SEQUENCE DESCRIPTION: SEQ ID NO:30:

CGGGATCCAA CAATGGGATG GAGCTGGATC TT   32

( 2 ) INFORMATION FOR SEQ ID NO:31:

( i ) SEQUENCE CHARACTERISTICS:
( A ) LENGTH: 164 base pairs
( B ) TYPE: nucleic acid
( C ) STRANDEDNESS: single
( D ) TOPOLOGY: linear ( i i ) MOLECULE TYPE: other nucleic acid
( A ) DESCRIPTION: oligonucleotide encoding an endoplasmic reticulum signal peptide from Kabat et al., 1987

( x i ) SEQUENCE DESCRIPTION: SEQ ID NO:31:

GATCCAACAA TGGGATGGAG CTGGATCTTT CTCTTCCTCC TGTCAGTTGT TACCCTACCT   60

CGACCTAGAA AGAGAAGGAG GACAGTGGAG CTGCAGGTGT CCATTGCCTA CTCGAGGGTA   120

CCGAGCTCCT CGACGTCCAC AGGTAACGGA TGAGCTCCGA TGGC   164

( 2 ) INFORMATION FOR SEQ ID NO:32:

( i ) SEQUENCE CHARACTERISTICS:
( A ) LENGTH: 10 amino acids
( B ) TYPE: amino acid
( C ) STRANDEDNESS: single
( D ) TOPOLOGY: linear ( i i ) MOLECULE TYPE: peptide ( v ) FRAGMENT TYPE: internal ( i x ) FEATURE:
( A ) NAME/KEY: Domain
( B ) LOCATION: 1..10
( D ) OTHER INFORMATION: /note="10 amino acid domain linker between light and heavy Fv fragments"

( x i ) SEQUENCE DESCRIPTION: SEQ ID NO:32:

Gly Gly Gly Gly Ser Gly Gly Gly Gly Ser
1               5                   10

( 2 ) INFORMATION FOR SEQ ID NO:33:

( i ) SEQUENCE CHARACTERISTICS:
( A ) LENGTH: 36 base pairs
( B ) TYPE: nucleic acid
( C ) STRANDEDNESS: single ( D ) TOPOLOGY: linear ( i i ) MOLECULE TYPE: other nucleic acid
    ( A ) DESCRIPTION: oligonucleotide KE147A28 used to make 36bp
    linker for pCIB4631

( x i ) SEQUENCE DESCRIPTION: SEQ ID NO:33:

GATCTGGTGG CGGTGGCTCG GGCGGTGGTG GGTCGC　　　　　　　　　　　　　　36

( 2 ) INFORMATION FOR SEQ ID NO:34:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: oligonucleotide KE182A28 used to make 36bp
    linker for pCIB4631

( x i ) SEQUENCE DESCRIPTION: SEQ ID NO:34:

TCGAGCGACC CACCACCGCC CGAGCCACCG CCACCA　　　　　　　　　　　　　　36

( 2 ) INFORMATION FOR SEQ ID NO:35:

( i ) SEQUENCE CHARACTERISTICS:
    ( A ) LENGTH: 26 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: PCR primer NC200 used to generate 700bp
    fragment containing the 3B1 single chain antibody coding
    sequence for fusion to PE40

( x i ) SEQUENCE DESCRIPTION: SEQ ID NO:35:

CGAAGCTTGA CATTGTGCTG ACCCAG　　　　　　　　　　　　　　　　　　　　26

( 2 ) INFORMATION FOR SEQ ID NO:36:

( i ) SEQUENCE CHARACTERISTICS:
    ( A ) LENGTH: 36 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: PCR primer NC202 used to generate 700bp
    fragment containing the 3B1 single chain antibody
    coding sequence for fusion to PE40

( x i ) SEQUENCE DESCRIPTION: SEQ ID NO:36:

GCCCTCTAGA AGCATGCCTG AGGAGACGGT GACTGA　　　　　　　　　　　　　　36

( 2 ) INFORMATION FOR SEQ ID NO:37:

( i ) SEQUENCE CHARACTERISTICS:
    ( A ) LENGTH: 29 base pairs
    ( B ) TYPE: nucleic acid
    ( C ) STRANDEDNESS: single
    ( D ) TOPOLOGY: linear ( i i ) MOLECULE TYPE: other nucleic acid
    ( A ) DESCRIPTION: PCR primer NC92 used to amplify antibody
    genes ( x i ) SEQUENCE DESCRIPTION: SEQ ID NO:37:

GTCTCGAGGA Y AT Y SWGMTS ACCCARTCT　　　　　　　　　　　　　　　　29

( 2 ) INFORMATION FOR SEQ ID NO:38:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: PCR primer NC130 used to amplify antibody genes ( x i ) SEQUENCE DESCRIPTION: SEQ ID NO:38:

GCAGATCTAG TTGGTGCAGC ATCAGCCCG        29

( 2 ) INFORMATION FOR SEQ ID NO:39:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: PCR primer NC91 used to amplify antibody genes ( x i ) SEQUENCE DESCRIPTION: SEQ ID NO:39:

GTCTCGAGCA GGTSMARCTG CAGSAGTCWG        30

( 2 ) INFORMATION FOR SEQ ID NO:40:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: PCR primer NC114 used to amplify antibody genes ( x i ) SEQUENCE DESCRIPTION: SEQ ID NO:40:

GCAGATCTAG ATCCAGGGGC CAGTGGATA        29

( 2 ) INFORMATION FOR SEQ ID NO:41:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: PCR primer NC111 used to amplify antibody genes ( x i ) SEQUENCE DESCRIPTION: SEQ ID NO:41:

GCAGATCTGC AGGAGACGAG GGGGAAGACA TT        32

( 2 ) INFORMATION FOR SEQ ID NO:42:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: PCR primer NC117 used to amplify antibody genes (x i) SEQUENCE DESCRIPTION: SEQ ID NO:42:

```
GCAGATCTGC AGCCAGGGAC CAAGGGATA                                              29
```

(2) INFORMATION FOR SEQ ID NO:43:

(i) SEQUENCE CHARACTERISTICS:
        (A) LENGTH: 22 amino acids
        (B) TYPE: amino acid
        (C) STRANDEDNESS: single
        (D) TOPOLOGY: linear (i i) MOLECULE TYPE: peptide (i i i) HYPOTHETICAL: NO (v) FRAGMENT TYPE: internal (i x) FEATURE:
        (A) NAME/KEY: Domain
        (B) LOCATION: 1..22
        (D) OTHER INFORMATION: /note="alternative domain linker between light and heavy Fv fragments"

(x i) SEQUENCE DESCRIPTION: SEQ ID NO:43:

```
Gly  Pro  Gly  Pro  Ser  Thr  Pro  Pro  Thr  Pro  Ser  Pro  Ser  Thr  Pro  Pro
 1              5                        10                       15

Thr  Pro  Ser  Gly  Pro  Gly
20
```

(2) INFORMATION FOR SEQ ID NO:44:

(i) SEQUENCE CHARACTERISTICS:
        (A) LENGTH: 357 base pairs
        (B) TYPE: nucleic acid
        (C) STRANDEDNESS: single
        (D) TOPOLOGY: linear (i i) MOLECULE TYPE: DNA (genomic)

(i i i) HYPOTHETICAL: NO (i v) ANTI-SENSE: NO (i x) FEATURE:
        (A) NAME/KEY: CDS
        (B) LOCATION: 1..357
        (D) OTHER INFORMATION: /note="14G1 heavy chain variable region from pCIB4635"

(x i) SEQUENCE DESCRIPTION: SEQ ID NO:44:

```
GAG  GTG  AAG  CTT  GTG  GAG  TCT  GGG  GGA  GGC  TTG  GTG  AGG  CCT  GGA  AAT      48
Glu  Val  Lys  Leu  Val  Glu  Ser  Gly  Gly  Gly  Leu  Val  Arg  Pro  Gly  Asn
 1              5                        10                       15

TCT  CTG  AAA  CTC  TCC  TGT  GTT  ACC  TCG  GGA  TTC  ACT  TTC  AGT  AAC  TAC      96
Ser  Leu  Lys  Leu  Ser  Cys  Val  Thr  Ser  Gly  Phe  Thr  Phe  Ser  Asn  Tyr
        20                       25                       30

CGG  ATG  CAC  TGG  CTT  CGC  CAG  CCT  CCA  GGG  AAG  AGG  CTG  GAG  TGG  ATT     144
Arg  Met  His  Trp  Leu  Arg  Gln  Pro  Pro  Gly  Lys  Arg  Leu  Glu  Trp  Ile
 35                       40                       45

GCT  GTA  ATT  ACA  CTC  AAA  TCT  GAT  AAT  TAT  GGA  ACA  ATT  TAT  GCA  GAA     192
Ala  Val  Ile  Thr  Leu  Lys  Ser  Asp  Asn  Tyr  Gly  Thr  Ile  Tyr  Ala  Glu
        50                       55                       60

TCT  GTG  AAA  GGC  AGA  TTC  ACC  ATT  TCA  AGA  GAA  GAT  TCA  GAA  AGC  AGC     240
Ser  Val  Lys  Gly  Arg  Phe  Thr  Ile  Ser  Arg  Glu  Asp  Ser  Glu  Ser  Ser
 65                       70                       75                       80

ATC  TAC  CTG  CAG  ATG  AAC  AGA  TTA  AGA  GAG  GAA  GAC  ACT  GCC  ACT  TAT     288
Ile  Tyr  Leu  Gln  Met  Asn  Arg  Leu  Arg  Glu  Glu  Asp  Thr  Ala  Thr  Tyr
 85                       90                       95
```

```
TAC  TGT  AGT  AGA  GGT  AGT  GAC  TGG  GGA  TTT  CCT  TAT  TGG  GGG  CAA  GGG      336
Tyr  Cys  Ser  Arg  Gly  Ser  Asp  Trp  Gly  Phe  Pro  Tyr  Trp  Gly  Gln  Gly
     100                 105                           110

ACT  CTG  GTC  ACT  GTC  TCT  GCA                                                    357
Thr  Leu  Val  Thr  Val  Ser  Ala
115
```

( 2 ) INFORMATION FOR SEQ ID NO:45:

( i ) SEQUENCE CHARACTERISTICS:
        ( A ) LENGTH: 119 amino acids
        ( B ) TYPE: amino acid
        ( D ) TOPOLOGY: linear ( i i ) MOLECULE TYPE: protein ( x i ) SEQUENCE DESCRIPTION: SEQ ID NO:45:

```
Glu  Val  Lys  Leu  Val  Glu  Ser  Gly  Gly  Gly  Leu  Val  Arg  Pro  Gly  Asn
 1                  5                        10                       15

Ser  Leu  Lys  Leu  Ser  Cys  Val  Thr  Ser  Gly  Phe  Thr  Phe  Ser  Asn  Tyr
     20                  25                       30

Arg  Met  His  Trp  Leu  Arg  Gln  Pro  Pro  Gly  Lys  Arg  Leu  Glu  Trp  Ile
35                       40                       45

Ala  Val  Ile  Thr  Leu  Lys  Ser  Asp  Asn  Tyr  Gly  Thr  Ile  Tyr  Ala  Glu
     50                       55                       60

Ser  Val  Lys  Gly  Arg  Phe  Thr  Ile  Ser  Arg  Glu  Asp  Ser  Glu  Ser  Ser
65                       70                       75                       80

Ile  Tyr  Leu  Gln  Met  Asn  Arg  Leu  Arg  Glu  Glu  Asp  Thr  Ala  Thr  Tyr
85                       90                       95

Tyr  Cys  Ser  Arg  Gly  Ser  Asp  Trp  Gly  Phe  Pro  Tyr  Trp  Gly  Gln  Gly
     100                 105                           110

Thr  Leu  Val  Thr  Val  Ser  Ala
115
```

( 2 ) INFORMATION FOR SEQ ID NO:46:

( i ) SEQUENCE CHARACTERISTICS:
        ( A ) LENGTH: 339 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 1..339
        ( D ) OTHER INFORMATION: /note="14G1 light chain variable
            region from pCIB4636"

( x i ) SEQUENCE DESCRIPTION: SEQ ID NO:46:

```
GAT  ATT  GTG  ATG  ACC  CAG  TCT  CCA  TCC  TCC  CTG  AGT  GTG  TCA  GCA  GGA       48
Asp  Ile  Val  Met  Thr  Gln  Ser  Pro  Ser  Ser  Leu  Ser  Val  Ser  Ala  Gly
 1                  5                        10                       15

GAG  AAG  GTC  ACT  ATG  AAC  TGC  AAG  TCC  AGT  CAG  AGT  CTG  TTA  AAT  AGT       96
Glu  Lys  Val  Thr  Met  Asn  Cys  Lys  Ser  Ser  Gln  Ser  Leu  Leu  Asn  Ser
     20                  25                       30

GGA  AAT  CAA  AAG  CAC  TAC  TTG  GCC  TGG  TAC  CAG  CAG  AAA  CCA  GGC  CAG      144
Gly  Asn  Gln  Lys  His  Tyr  Leu  Ala  Trp  Tyr  Gln  Gln  Lys  Pro  Gly  Gln
35                       40                       45
```

| | | | | | | | | | | | | | | | | |
|---|---|---|---|---|---|---|---|---|---|---|---|---|---|---|---|---|
| CCT | CCT | AAA | CTG | TTG | ATC | TAC | GGG | GCA | TCC | ACT | AGG | GAA | TCT | GGG | GTC | 192 |
| Pro | Pro 50 | Lys | Leu | Leu | Ile | Tyr 55 | Gly | Ala | Ser | Thr | Arg 60 | Glu | Ser | Gly | Val | |
| CCT | GAT | CGC | TTC | ACA | GGC | AGT | GGG | TCT | GGA | ACC | GAT | TTC | ACT | CTT | ACC | 240 |
| Pro 65 | Asp | Arg | Phe | Thr | Gly 70 | Ser | Gly | Ser | Gly | Thr 75 | Asp | Phe | Thr | Leu | Thr 80 | |
| ATC | AGC | AGT | GTG | CAG | GCT | GAA | GAC | CTG | GCA | GTT | TAT | TTC | TGT | CAG | AAT | 288 |
| Ile 85 | Ser | Ser | Val | Gln | Ala 90 | Glu | Asp | Leu | Ala | Val 95 | Tyr | Phe | Cys | Gln | Asn | |
| GAT | CGT | AGT | TAT | CCG | TTC | ACA | TTC | GCC | TCG | GGG | ACA | AAG | TTG | GAA | ATA | 336 |
| Asp | Arg 100 | Ser | Tyr | Pro | Phe | Thr 105 | Phe | Ala | Ser | Gly | Thr 110 | Lys | Leu | Glu | Ile | |
| AAA | | | | | | | | | | | | | | | | 339 |
| Lys | | | | | | | | | | | | | | | | |

( 2 ) INFORMATION FOR SEQ ID NO:47:

( i ) SEQUENCE CHARACTERISTICS:
        ( A ) LENGTH: 113 amino acids
        ( B ) TYPE: amino acid
        ( D ) TOPOLOGY: linear ( i i ) MOLECULE TYPE: protein ( x i ) SEQUENCE DESCRIPTION: SEQ ID NO:47:

| | | | | | | | | | | | | | | |
|---|---|---|---|---|---|---|---|---|---|---|---|---|---|---|
| Asp 1 | Ile | Val | Met | Thr 5 | Gln | Ser | Pro | Ser | Ser 10 | Leu | Ser | Val | Ser | Ala 15 | Gly |
| Glu | Lys 20 | Val | Thr | Met | Asn 25 | Cys | Lys | Ser | Ser | Gln 30 | Ser | Leu | Leu | Asn | Ser |
| Gly 35 | Asn | Gln | Lys | His | Tyr 40 | Leu | Ala | Trp | Tyr | Gln 45 | Gln | Lys | Pro | Gly | Gln |
| Pro | Pro 50 | Lys | Leu | Leu | Ile | Tyr 55 | Gly | Ala | Ser | Thr | Arg 60 | Glu | Ser | Gly | Val |
| Pro 65 | Asp | Arg | Phe | Thr | Gly 70 | Ser | Gly | Ser | Gly | Thr 75 | Asp | Phe | Thr | Leu | Thr 80 |
| Ile 85 | Ser | Ser | Val | Gln | Ala 90 | Glu | Asp | Leu | Ala | Val 95 | Tyr | Phe | Cys | Gln | Asn |
| Asp | Arg 100 | Ser | Tyr | Pro | Phe | Thr 105 | Phe | Ala | Ser | Gly | Thr 110 | Lys | Leu | Glu | Ile |

Lys ( 2 ) INFORMATION FOR SEQ ID NO:48:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: PCR primer DB91 used to amplify antibody genes ( i i i ) HYPOTHETICAL: NO ( i v ) ANTI-SENSE: NO ( x i ) SEQUENCE DESCRIPTION: SEQ ID NO:48:

ACGTCTCGAG GARGTGAAGC TKRWKGARWC TG    32

( 2 ) INFORMATION FOR SEQ ID NO:49:

( i ) SEQUENCE CHARACTERISTICS:
        ( A ) LENGTH: 34 base pairs ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: PCR primer DB114 used to amplify antibody
            genes ( i i i ) HYPOTHETICAL: NO ( i v ) ANTI-SENSE: NO ( x i ) SEQUENCE DESCRIPTION: SEQ ID NO:49:

CAATTCGCAT ATGAGATCCA GGGGCCAGTG GATA                    3 4

ANTIBODIES WHICH BIND TO INSECT GUT PROTEINS AND THEIR USE

This is a divisional application of Ser. No. 08/267,641, filed Jun. 28, 1994.

FIELD OF THE INVENTION

The invention is drawn to antibodies that bind to insect gut proteins and their use, particularly their use in mating new hybrid toxin molecules.

BACKGROUND OF THE INVENTION

Control of various pests through the use of biological molecules has been possible in only a limited number of cases. The best known examples of biological molecules with pesticidal uses are the δ-endotoxins from *Bacillus thuringiensis* (Bt). Various strains of Bt are known which produce insecticidal proteins, the δ-endotoxins, during sporulation. Some of these δ-endotoxins have useful insecticidal activities against different insect pests. However, use of the δ-endotoxins is limited because they are active against only a very few of the many insect pests.

The limited specificity of the Bt endotoxins is dependent, at least in part, on both the activation of the toxin in the insect gut (Haider, M. Z. et al., 1986, Eur. J. Biochem, 156:531–540) and its ability to bind to specific receptors present on the insect's midgut epithelial cells (Hofmann, C. P. et al., 1988, PNAS 85:7844–7848). Among the factors which prevent activity of a particular Bt δ-endotoxin against a specific insect is the lack of appropriate receptors in the insect gut or lack of affinity of the δ-endotoxin for the receptors which may be present, thus resulting in no binding of the δ-endotoxin to the brush border membranes. Therefore, the ability to control a specific insect pest using Bt δ-endotoxins at present depends on the ability to find an appropriate δ-endotoxin with the desired range of activity. In many cases, no such δ-endotoxin is known, and it is not certain that one even exists. For example, thousands of Bt strains have been screened for activity against western corn rootworm (WCRW), a major pest of maize. However, to date there are no reports of strains of Bt which produce a δ-endotoxin that is highly effective against WCRW.

Individual δ-endotoxins typically have a very narrow spectrum of activity, each being active against only one or a few insect pests. Moreover, the δ-endotoxins have been shown to be active against only a few members of but a small number of Orders of insects. The ability to produce additional proteins with unique pesticidal activities creates more options for the control of agricultural pests, particularly insects, using biological molecules with a high level of safety for non-target organisms. Thus, there is a need for binding proteins which can be designed to target a particular insect pest.

SUMMARY OF THE INVENTION

The present invention is drawn to antibodies, monoclonal antibodies or fragments thereof which bind to brush border membrane vesicles of insect gut and the gene or genes which encode these proteins. The antibodies bind to proteins in the gut of a target insect but do not bind to mammalian brush border membranes or to plant microsomes. The antibodies and the genes encoding them find use in constructing hybrid-toxins for control of insect pests. The antibodies and genes also find use in receptor cloning.

BRIEF DESCRIPTION OF THE FIGURE

FIG. 1: Western blot analysis of binding of monoclonal antibodies to corn rootworm brush border membrane vesicles after electrophoresis on acrylamide gels. Antibodies from cell lines 3B1, 2B5, 17F6 and 10B6 were used in the analysis. MW=Molecular weight standards.

DETAILED DESCRIPTION OF THE INVENTION

Antibodies and monoclonal antibodies, including fragments thereof which are capable of binding with the specificity of the antibody or monoclonal antibody, to proteins found in the insect gut are provided. Such antibodies bind to insect gut cells but do not bind to mammalian brush border membrane vesicles (BBMVs), nor to plant microsomes.

The antibodies of the invention include polyclonal and monoclonal antibodies as well as fragments thereof which retain their ability to bind to proteins found in the insect gut. An antibody, monoclonal antibody, or fragment thereof is said to be capable of binding a molecule if it is capable of specifically reacting with the molecule to thereby bind the molecule to the antibody, monoclonal antibody, or fragment thereof. The term "antibody" (Ab) or "monoclonal antibody" (Mab) is meant to include intact molecules as well as fragments or binding regions or domains thereof (such as, for example, Fab and F(ab)$_2$ fragments) which are capable of binding hapten. Such fragments are typically produced by proteolytic cleavage, such as papain or pepsin. Alternatively, hapten-binding fragments can be produced through the application of recombinant DNA technology or through synthetic chemistry.

Methods for the preparation of the antibodies of the present invention are generally known in the art. For example, see *Antibodies, A Laboratory Manual*, Ed Harlow and David Lane (eds.) Cold Spring Harbor Laboratory, N.Y. (1988), as well as the references cited therein. Standard reference works setting forth the general principles of immunology include: Klein, J. *Immunology: The Science of Cell-Noncell Discrimination*, John Wiley & Sons, N.Y. (1982); Dennett, R., et al. *Monoclonal Antibodies, Hybridoma: A New Dimension in Biological Analyses*, Plenum Press, N.Y. (1980); and Campbell, A. "Monoclonal Antibody Technology," In *Laboratory Techniques in Biochemistry and Molecular Biology*, Vol. 13, Burdon et al. (eds.), Elsevier, Amsterdam (1984). See also, U.S. Pat. Nos.: 4,609,893; 4,713,325; 4,714,681; 4,716,111; 4,716,117; and 4,720,459.

The antibody and monoclonal antibodies of the present invention can be prepared by utilizing insect guts, particularly insect brush border membranes, as the antigen. Such insect gut membranes can be prepared by methods known in the art Generally, brush border membranes can be isolated from insect larvae by dissection of guts and homogenization followed by calcium chloride precipitation of membranes. See, for example, Wolfersberger (1986) Comp. Biochm. Physiol. 86A:301–308.

It is recognized that following the methods described herein, antibodies specific for a particular target insect can be prepared. By target insect is meant an insect in which the antibodies of the present invention will bind to protein or proteins present in the gut. That is, antibodies can be prepared that are capable of binding proteins present in the gut of only the target insect.

The target insect encompasses arty insect including insects selected from the orders Coleoptera, Diptera, Hymeneoptera, Lepidoptera, Mallophaga, Homoptera, Hemiptera, Orthroptera, Thysanoptera, Dermaptera, Isoptera, Anoplura, Siphonaptera, Trichoptera, etc. Thus, any insect pest can be selected and antibodies made which are specific to that insect. Of particular interest are insect pests for which there is no Bt protein which is capable of binding and killing, such as western corn rootworm.

The antibody and monoclonal antibody producing cell lines of the invention are a subset of all monoclonal antibodies produced when insect brush border membrane vesicles (BBMVs) are used as antigen for the production of MAb lines. The binding characteristics of the desired monoclonal antibody producing cell lines are determined by differentially screening all of the various monoclonal antibodies raised against the BBMVs of the target insect.

The differential screen of the present invention identifies the antibody lines which also bind mammalian BBMVs and/or microsomes of plants. MAb Cell lines which bind to mammalian BBMVs or to plant microsomes are discarded. A differential screen can also identify Mab cell lines which bind BBMV of insects in species other than the target insect. Thus, the antibodies of the invention are those which demonstrate highly selective binding for only target insects, especially for the gut of a target insect.

The subset of MAb lines which possess the desired binding specificity can be used as a source of messenger RNA for cloning of the cDNA for the particular monoclonal antibody. Antibody genes can be cloned from hybridoma cells using primers to conserved DNA sequences within the constant regions and the framework regions of the variable regions. This can be followed by amplification of the DNA for cloning using the polymerase chain reaction (PCR). A database of mouse heavy chain and light chain sequences complied by Kabat et al. has been successfully used to generate both isotype specific and degenerate prim for cloning antibody genes (Kabat, E. A. et al., 1987, U.S. Dept Health and Human Services, U.S. Government Printing Offices and Jones, S. T. and Bendig, M., 1991, Bio/technology 9:88–89). Additionally, there is a wealth of knowledge concerning the cloning of smaller fragments of antibodies which possess the binding properties of the original antibody.

The cloned DNA can then be sequenced by methods known in the art. See, for example, Sambrook et al., Molecular Cloning: A Laboratory Manual, 2nd. Edition, Cold Spring Harbor Laboratory Press, N.Y. (1989) vol. 1–3, and the references cited therein. From the nucleic acid sequence, the protein sequence of the binding region from the selected MAb can be deduced.

The antibodies and monoclonal antibodies of the invention find use in the production of hybrid toxin molecules. By "hybrid toxin molecules" or "hybrid toxins" is intended, fusion proteins or immunotoxins, which comprise a monoclonal antibody or antibody fragment operably linked to a toxin moiety and which is capable of binding to the gut of an insect. That is, when linked, the monoclonal antibody or antibody fragment retains its binding properties and the toxin moiety retains its cytotoxic properties.

A number of cytotoxic proteins can be utilized as the toxin moiety. These include but are not limited to Bacillus toxins, including endotoxins and vegetative insecticidal proteins. See for example U.S. application Ser. No. 08/037,057, filed Mar. 25, 1993 and U.S. application Ser. No. 07/951,715 filed Sep. 25, 1992, herein incorporated by reference. Other toxins include catalytic ribosome inactivators such as gelonin, Pseudomonas exotoxin A or phytolaccin, (the structure of Pseudomonas exotoxin has been well characterized in Chaudhary et al., (1990) J. Biol. Chem. 265:16303–16310); cell metabolism disrupters, such as ribonucleases, (see, for example, Mariani et al. (1990) Nature 347:737–741); Barnase toxin (or PE-Bar), a chimeric toxin derived from Pseudomonas exotoxin A and a ribonuclease, (see, Prior et al. (1991) Cell 64:1017–1023); hydrophilic peptides that create pores in membranes (see, Frohlich and Wells (1991) Int. J. Peptide Protein Res. 37:2–6); etc.

The hybrid toxin molecules of the present invention therefore contain a region which allows binding of the molecule to insect guts (antibody region) as well as a toxic region to effect killing of the targeted cell and ultimately the targeted insect. By utilizing the monoclonal antibodies or fragments thereof in the hybrid toxins, the hybrid toxins bind to the gut of a target insect and thereby exert a toxic effect on only that insect. The binding characteristics of such hybrid toxins are derived from the MAb binding region while the toxic effect of such hybrid toxins is derived from the toxic moiety used.

Methods for linking the antibody or antibody fragments to the toxins are known in the art. Such methods include linkers used in single chain antibody immunotoxins (Chaudhary et al. (1989) Nature 339:394–397; Chaudhary et al. (1990) PNAS 87:9491–9494; Batra et al. 1991, Mol. and Cellular Biol. 11:2200–2205; Brinkmann, et al. (1991), PNAS 88:8616–8620; Brinkmann et al. (1992) PNAS 89:3075–3079; Whitlow et al. (1993) Protein Engineering 6:989–995). One particularly useful linker is based on the human IgA1 hinge region as reported by Hallewell et al. (1989) J. Biol. Chem. 264:5260–5268 and described in SEQ ID NO:43.

The activity of the hybrid toxin molecules may depend on several factors which can be optimized. The activity can be assayed using protein produced by transiently expressing maize protoplasts. In this manner, maize protoplasts expressing the hybrid toxins can be incorporated into insect diet for activity assays. For general insect assays, see Marrone (1985) J. Econ. Entomolo. 78:290–293, Macintosh el. al. (1990) J. of Invertebrate Pathology 56:258–266 and the references cited therein.

Thus, hybrid toxin constructs can be tested for insecticidal activity against the target pest of interest. Those constructs exhibiting activity can be further developed for agricultural use.

It is further recognized that various constructs of hybrid toxins can be generated. For example, the hybrid toxin could be encoded by two expression cassettes which respectively encode the light and heavy chains of the antibody molecule. This binary hybrid toxin can then be assembled in vivo using the normal processing machinery of the cell to create the antibody binding site. The toxin moiety of the hybrid can be operably linked to the N or C terminal of the light or heavy chain or alternatively could replace any or part of the constant regions of either chains. The toxin moiety could also be inserted within a constant region or between constant regions of the antibody chains. Such constructions can be made by standard molecular techniques. See, for example Sambrook et al., Molecular Cloning: A Laboratory Manual, 2nd. Edition, Cold Spring Harbor Laboratory Press, N.Y. (1989) vol. 1–3 and the references cited therein.

The hybrid toxins of the present invention, including binary toxins, can be produced in plants. In this manner, the antibody genes can be cloned and expressed in plants in such a manner that functional antibodies are assembled. See, for example, Hiatt et al. (1989) Nature 342:76–78 During et al. (1990) J. Plant Molecular Biology 15:281–293 and PCT Application WO 91/06320. Levels of bivalent antibody expression have been reported to be as high as 1% of the soluble protein in tobacco. It is recognized that as well as antibody molecules, antibody fragments such as Fab and Fv fragments, can be utilized. The smaller Fab and Fv antigen-binding fragments (12 kDa–50 kDa) have been shown to retain full binding affinity. Single chain Fv fragments (scFv), in which Vh and Vl domains are linked by a hydrophilic and flexible peptide, have been used successfully to target enzymes and toxins to specific cells (Bird (1988) Science 423:423–426 and Huston (1988) PNAS 85:5879–5883). Single Vh domains (Dabs) and single complementary determining regions as small as 20 amino acids (aa) called minimal recognition units (mru) have also been used for antigen binding (Ward (1989) Nature 341:544–546 and Taub (1989) J. Biol. Chem 264:259–265 and Williams (1989) PNAS 86:5537–5541). The use of these antibody fragments provides the option of reducing the insect specific binding domain derived from a MAb to a very small size.

DNA fragments encoding antibodies, or regions of antibodies, which bind to the gut of insects are also encompassed by the present invention. In a preferred embodiment, these DNA fragments encode binding regions which are derived from monoclonal antibodies raised against BBMVs of a desired target insect and screened to ensure they do not bind to mammalian BBMV or to plant microsomes. Such DNA fragments can be used in the construction of genes encoding novel hybrid toxin molecules which are discussed above.

DNA sequences encoding the toxin moiety of the hybrid toxins are known in the art. See, Lamb et al. (1985) Eur. J. Biochem. 148:275–170 (Ricin); Gray et al. (1984) PNAS 81:2645–2649 (Pseudomonas toxin DNA Sequence); Hindley and Berry (1988) Nuc. Acids Res. 16:4168 (*B. sphaericus* toxin gene); Bauman et al. (1988) J. Bacteriol 170:2045–2050, Bauman et al. 1987) J. Bacteriol 169:4061–4067, Berry and Hindley (1987) Nucleic Acids Res. 15:5891, Berry et al. (1989) Nucleic Acids Res. 17:7516 (*B. sphaericus*); WO 9309130-A (gelonin); EP 466222-A, U.S. Pat. No. 5,128,460 (ribosome-activating protein); EP 412911-A (barnase); Heernstadt et al. (1987) Gene 57:37–46 (cryIIIA); Brizzard and Whiteley (1988) Nucleic Acids Res 16:2723–2724 (cryIB); and Geiser et al. (1986) Gene 48:109–118 (cryIA(b)). See also Porter et al. (1993) Microbiological Reviews 57:838–861; Hofte and Whiteley (1989) Microbiological Reviews 53:242–255; and U.S. application Ser. No. 07/951,715 filed Sep. 25, 1992.

The hybrid toxin genes of the invention can be optimized for enhanced expression in plants. See, for example U.S. application Ser. No. 07/951,715; EPA 0359472; EPA 0385962; WO 91/16432; Perlak et al. (1991) Proc. Natl. Acad. Sci. USA 88:3324–3328;and Murray (1989) Nucleic Acids Research 17:477–498. In this manner, the genes can be synthesized utilizing plant preferred codons. That is, the preferred codon for a particular host is the single codon which most frequently encodes that amino acid in that host. The maize preferred codon, for example, for a particular amino acid may be derived from known gene sequences from maize. Maize codon usage for 28 genes from maize plants is found in Murray, (1989), Nucleic Acids Research 17:477–498, the disclosure of which is incorporated herein by reference. Synthetic genes could also be made based on the distribution of codons a particular host uses for a particular amino acid.

Following this approach, the nucleotide sequences can be optimized for expression in any plant. It is recognized that all or any part of the gene sequence may be optimized or synthetic. That synthetic, partially optimized, or native sequences may also be used.

Methods for the transformation of plant cells and regeneration of transformed plants are well known in the art. Generally, for the introduction of foreign DNA into plants Ti plasmid vectors have been utilized as well as direct DNA uptake, liposomes, electroporation, micro-injection, and the use of microprojectiles. Such methods have been published. See, for example, Guerche et al., (1987) Plant Science 52:111–116; Neuhause et al., (1987) Theor. Appl. Genet. 75:30–36; Klein et al., (1987) Nature 327:70–73; Howell et al., (1980) Science 208:1265; Horsch et al., (1985) Science 227: 1229–1231; DeBlock et al., (1989) Plant Physiology 91:694–701; Methods for Plant Molecular Biology (Weissbach and Weissbach, eds.) Academic Press, Inc. (1988); and Methods in Plant Molecular Biology (Schuler and Zielinski, eds.) Academic Press, Inc. (1989). See also U.S. patent application Ser. No. 08/008,374 herein incorporated by reference. See also, EPA 0193259 and EPA 0451878A1. It is understood that the method of transformation will depend upon the plant cell to be transformed.

It is further recognized that the components of an expression cassette containing the sequence of interest may be modified to increase expression in the plant or plant cell For example, truncated sequences, nucleotide substitutions or other modifications may be employed. See, for example Perlak et al. (1991) Proc. Natl. Acad. Sci. USA 88:3324–3328; Murray et al. (1989) Nucleic Acids Research 17:477–498; and WO 91/16432.

The construct may also include any other necessary regulators such as terminators, (Guerineau et al., (1991), Mol. Gen. Genet., 226:141–144; Proudfoot, (1991), Cell, 64:671–674; Sanfacon et al., (1991), Genes Dev., 5:141–149; Mogen et al., (1990), Plant Cell 2:1261–1272; Munroe et al., (1990), Gene, 91:151–158; Ballas et al., (1989), Nucleic Acids Res., 17:7891–7903; Joshi et al., (1987), Nucleic Acid Res., 15:9627–9639); plant translational consensus sequences (Joshi, C. P., (1987), Nucleic Acids Research, 15:6643–6653), introns (Luehrsen and Walbot, (1991), Mol. Gen. Genet., 225:81–93) and the like, operably linked to the nucleotide sequence. It may be beneficial to include 5' leader sequences in the expression cassette construct. Such leader sequences can act to enhance translation. Translational leaders are known in the art and include:

Picornavirus leaders, for example, EMCV leader (Encephalomyocarditis 5' noncoding region) (Elroy-Stein, O., Fuerst, T. R., and Moss, B. (1989) PNAS USA 86:6126–6130);

Potyvirus leaders, for example, TEV leader (Tobacco Etch Virus) (Allison et al., (1986); MDMV leader (Maize Dwarf Mosaic Virus); Virology, 154:9–20), and Human immunoglobulin heavy-chain binding protein (BiP), (Macejak, D. G., and Sarnow, P., (1991), Nature, 353:90–94;

Untranslated leader from the coat protein mRNA of alfalfa mosaic virus (AMV RNA 4), (Jobling, S. A., and Gehrke, L., (1987), Nature, 325:622–625;

Tobacco mosaic virus leader (TMV), (Gallie, D. R. et al., (1989), Molecular Biology of RNA, pages 237–256; and Maize Chlorotic Mottle Virus leader (MCMV) (Lommel, S. A. et al., (1991), Virology, 81:382–385. See also, Della-Cioppa et al., (1987), Plant Physiology, 84:965–968.

A plant terminator may be utilized in the expression cassette. See, Rosenberg et al., (1987), Gene, 56:125; Guerineau et al., (1991), Mol. Gen. Genet., 226:141–144; Proudfoot, (1991), Cell 64:671–674; Sanfacon et al., (1991), Genes Dev., 5:141–149; Mogen et al., (1990), Plant Cell 2:1261–1272; Munroe et al., (1990), Gene, 91:151–158;Ballas et al., (1989), Nucleic Acids Res., 17:7891–7903; Joshi et al., (1987), Nucleic Acid Res., 15:9627–9639.

For tissue specific expression, the nucleotide sequences of the invention can be operably linked to tissue specific promoters. See, for example, U.S. application Ser. No. 07/951,715 herein incorporated by reference.

The hybrid toxin proteins of the invention may be used for protecting agricultural crops and products from pests. Alternatively, a gene encoding the hybrid toxin may be introduced via a suitable vector into a microbial host, and said host applied to the environment or plants or animals. Microorganism hosts may be selected which are known to occupy the "phytosphere" (phylloplane, phyllosphere, rhizosphere, and/or rhizoplana) of one or more crops of interest. These microorganisms are selected so as to be capable of successfully competing in the particular environment with the wild-type microorganisms provide for stable maintenance and expression of the gene expressing the polypeptide pesticide, and, desirably, provide for improved protection of the pesticide from environmental degradation and inactivation.

Such microorganisms include bacteria, algae, and fungi. Of particular interest are microorganisms, such as bacteria, e.g., Bacillus, Caulobacter, Agmenellum, Pseudomonas, Erwinia, Serratia, Klebsiella, Xanthomonas, Streptomyces, Rhizobium, Rhodopseudomonas, Methylius, Agrobacterium, Acetobacter, Lactobacillus, Arthrobacter, Azotobacter, Leuconostoc, and Alcaligenes; fungi, particularly yeast, e.g., Saccharomyces, Cryptococcus, Kluyveromyces, Sporobolomyces, Rhodotorula, and Aureobasidium. Of particular interest are such phytosphere bacterial species as *Pseudomonas syringae, Pseudomonas fluorescens, Serratia marcescens, Acetobacter xylinum,* Agrobacteria, *Rhodopseudomonas spheroides, Xanthomonas campestris, Rhizobium melioti, Alcaligenes entrophus, Clavibacter xyli* and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces rosues, S. odorus, Kluyveromyces veronae*, and Aureobasidium pollulans. Of particular interest are the pigmented microorganism.

A number of ways are available for introducing a gene expressing the hybrid toxin into the microorganism host under conditions which allow for stable maintenance and expression of the gene. For example, expression cassettes can be constructed which include the DNA constructs of interest operably linked with the transcriptional and translational regulatory signals for expression of the DNA constructs, and a DNA sequence homologous with a sequence in the host organism, whereby integration will occur, and/or a replication system which is functional in the host, whereby integration or stable maintenance will occur.

Transcriptional and translational regulatory signals include but are not limited to promoter, transcriptional initiation start site, operators, activators, enhancers, other regulatory elements, ribosomal binding sites, an initiation codon, termination signals, and the like. See, for example, U.S. Pat. No. 5,039,523; U.S. Pat. No. 4,853,331; EPO 0480762A2; Sambrook et al. supra; Molecular Cloning, a Laboratory Manual, Maniatis et al. (eds) Cold Spring Harbor Laboratory, Cold Spring Harbor, N.Y. (1982); Advanced Bacterial Genetics, Davis et al. (eds.) Cold Spring Harbor Laboratory, Cold Spring Harbor, N.Y. (1980); and the references cited therein.

The following examples are offered by way of illustration and are not truant to be limiting on the invention described herein.

EXPERIMENTAL

Example 1: Monoclonal Antibody Development

Immunization:

Appropriate quantifies of the antigen (approximately 50 micrograms of corn rootworm BBMVs) were emulsified in a non-oil based adjuvant and used to immunize a group of ten Balb/c mice. Mice were given booster immunizations at biweekly intervals. Seven days following the third booster injection, serum samples were taken from the mice, and the relative serum antibody tilers determined by an enzyme-linked immunosorbent assay (ELISA), as described below. A group of four mice with the highest riters were given a final regimen of low-dose antigert boosters (approximately one-tenth of the dosage used during the regular immunization) over a period of three days, and used as spleen donors in fusions as described below.

Fusion:

Four mice with specific antibody titers of >1:5,000 were selected for two fusions. Spleens were aseptically excised, mechanically dissociated and the lymphocytes isolated as follows. The red blood cells were lysed by incubation with a 0.155M solution of ammonium chloride in 0.017 TRIZMA base, pH 7.2. The cells were washed twice with phosphate buffered saline (PBS) and lymphocytes further purified by running a density gradient centrifugation as follows. Cells were carefully layered on a Ficoll solution of specific gravity 1.065 (Van Mourik et al., Meth. in Enzymology, 121:174–182 (1986)) and centrifuged at 450×g for 20 minutes. The pellet that contains cells of density greater than 1.065 is greatly enriched in lymphocytes, and was fused with myeloma cells.

A polyethylene glycol-mediated fusion was performed using isolated lymphocytes and a Balb/c-derived HGPRT (Hypoxanthine Guanine Phosphoribosyl Transferase) deficient SP2/0 plasmacytoma cell line. Lymphocytes were mixed with myeloma cells at a ratio of 4:1. The cell mixture was thoroughly mixed, centrifuged and the fusion carried out as follows (Oi et al. in Selected Methods in Cellular Immunology eds. Michell, B. B. and Shiigi, S. M. (Freeman, San Francisco) 351–371 (1980), Fazekas et al., J. Immunol. Meth., 35:1–21 (1980)). The cell pellet was carefully suspended in 1 ml of a 50% polyethylene glycol (PEG) with constant stirring over a period of one minute. The PEG concentration was gradually reduced by diluting the cells with serum free RPMI media. After the fusion, the fused cells were pelleted at 80×g for 5 minutes, resuspended and plated into 96 well plates at a density of $10^5$ to $10^6$ total cells per well. Spleen feeder cells, prepared by treating non-immune splenocytes with 20 μg/ml mitomycin C were added to provide supplemental growth factors to the fused cells. For the next several days, the hybridomas were selected by using HAT (Hypoxanthine Aminopterin Thymidine) media that contained 17.6 μg/ml of aminopterin. Growing colonies were seen under an inverted microscope as early as 3 or 4 days after fusion. However, macroscopic colonies were not visible until 10 to 14 days after fusion. At this stage, the supernatants of each well were assayed for specific antibody secretion.

Screening:

Upon detection of viable hybridoma colonies surviving HAT selection, the supernatants were screened using an enzyme-linked immunosorbent assay (ELISA) (Engvall, Meth. Enzymology, 70:419 (1980), Engvall et al., Immunochemistry, 8:871 (1971)). Very briefly, hybridoma supernatants were incubated in wells of 96-well microtiter plates bearing approximately 500 nanograms per well of the antigen. After appropriate washing steps, bound antibodies were identified using a goat anti-mouse second antibody conjugated to horseradish peroxidase (HRP). After additional washing steps, the enzyme activity in each well was quantified with chromogenic substrate. The resultant absorbance at 492 nm (OD492) was measured with an automated ELISA reader to identify the positive colonies. Hybridoma lines with strong binding to the corn rootworm BBMVs were further screened by three additional ELISA screens to eliminate those monoclonals which bind to either mammalian or plant proteins. More specifically, ELISAs were performed using rabbit intestinal brush border membranes and maize leaf and root microsomal membrane preparations. An ELISA screen to identify lines with cross-reactivity to European corn borer BBMVs was also included.

Hybridoma colonies which secreted antibodies which bound to the corn rootworm BBMV antigen and not to the mammalian and plant proteins were cloned as described below.

Cloning:

In this phase, hybridomas which secrete antibodies with apparent specificity for the antigen were expanded and cloned in 96 well plates at target concentrations of 0.5, 1 and 5 cells/well. Growth factors (Sugasawara et al., J. Immunol. Meth., 79:276–275 (1985)) were provided to promote hybridoma cells grown from limited densities. After 2–3 weeks, when the clones were large enough, positive clones were identified again using the ELISAs as described under "Screening." Representative clones were then expanded for antibody production.

Ascites Production:

Large-scale production of appropriate monoclonal antibodies was accomplished by growing the hybridomas as ascites tumors in pristane-primed Balb/c mice (Brodeur et al., J. Immunol. Meth., 71:265–272 (1984)). Ascites fluid was pooled, and the antibodies partially purified from dialyzed ascites by Protein A chromatography. The resultant antibody preparations were aliquoted and frozen.

Cell lines which produce monoclonal antibodies useful in the present invention are described in Table 1. The hybridoma cell lines whose ATCC designations are indicated in Table 1 were deposited with the American Type Culture Collection on Apr. 19, 1994.

TABLE 1

CRW BBMV MONOCLONAL LINES

| Cell line | ECB Crossreact | Western Blot | Isotype | ATCC Designation |
|---|---|---|---|---|
| 1A4 | yes | 2 CRW bands | IgM-k | |
| 1A11 | no | 2 CRW bands | IgM-k | |
| 1F51 | yes | 2 CRW bands | IgM-k | |
| 2B5 | yes | 2 CRW bands | IgM-k | HB 11619 |
| 3B1 | no | 1 CRW band | IgGl-k | HB 11617 |
| 7G6 | no | >5 bands | IgM-k | |
| 10A1 | no | no signal | IgM-k | |
| 10B6 | no | >5 bands C | IgG3-K | HB 11618 |
| 10F9 | no | >5 bands B | IgM-k | |
| 12G4 | no | not done | IgM-k | |
| 14G1 | no | >5 bands | IgG2B-k | |
| 17F6 | no | >5 bands A | IgG1-k | HB 11620 |
| 17H6 | no | >5 bands A | IgG2A-k | |
| 18A7 | no | >5 bands B | IgG1-k | |
| 16E4 | yes | >5 bands | IgM | HB 11616 |

Example 2: Isolation of Brush Border Membranes Vehicles (BBMV)

Isolation of Corn Rootworm BBMV:

Vesicles were prepared based on the method of Wolfersberger et al., Comp. Biochem. Physiol. 86A:301–308 (1987) as modified by English and Readdy (Insect Biochem. 19;145–152 (1989)). The guts of third instar corn rootworm larvae were homogenized in ice-cold 50 mM sucrose, 2 mM Tris-Cl (pH 7.4), 0.1 mM phenylmethylsulfonyl fluoride using a Potter-Elvenhem homogenizer. Calcium chloride was added to 10 mM and the homogenate stirred on ice for 15 min. The homogenate was centrifuged at 4,300×g for 10 min at 4° C., and the pellet discarded. The supernatant was centrifuged at 27,000×g for 10 min, and the pellet resuspended in 0.32M sucrose. The suspension was passed through a 27-gauge needle and stored at −70° C.

Isolation of European Cornborer BBMV:

Guts were excised from fifth instar European corn borer (ECB) and cut longitudinally to remove the food contents and peritrophic membrane. Isolation of (ECB) BBMVs were performed using the methods described above.

Isolation of Plant Microsomes:

Leaf or root tissue from corn plants (grown 72 hrs in dark at 28° C.) were ground up with a mortar and pestle in an equal volume of 0.3M potassium phosphate pH 7.4, 5 mM DTT, and 1% (w/v) PVPP. The mixture was strained through four layers of cheesecloth, followed by centrifugation at 10,000×g for 15 min. The supernatant was centrifuged at 100,000×g for 60 min and the pellet resuspended in 0.1M potassium phosphate pH 7.4.

Isolation of Mammalian Intestinal BBMV:

Mammalian brush border membranes were prepared from the mucosal surface of rabbit duodenum and stroma (Kessler et al. BBA 506:136–154 (1978)) using a similar process to the isolation of brush border membrane vesicles from insect guts. The mucosal lining of fresh rabbit duodenum and lower stomach was washed and the mucosal layer separated from the underlying stroma. The material was suspended in a 10-fold volume of ice-cold 50 mM sucrose, 0. 1 mM PMSF, 2 mM Tris-HCl (pH7.4) and homogenized with 15 strokes on ice. Calcium chloride was added to a final concentration of 10 mM, and the mixture stirred on ice for 15 min. The homogenate was centrifuged at 4300×g for 10 min at 4° C. The supernatant was harvested and centrifuged at 27,000×g for 10 min. The pellet was resuspended in 0.32M sucrose and frozen at −70° C.

Example 3: Characterization of CRW BBMV Monoclonal Lines

Monoclonal lines with strong binding to CRW BBMVs based on ELISA were further screened to select clones with no cross-reactivity to either maize or mammalian microsomes. The additional ELISAs were performed using corn leaf and root microsomes and rabbit intestinal membrane vesicles. All lines were simultaneously screened against European corn borer BBMV proteins. From seventy-eight lines screened, eleven specific to corn rootworm were isolated. In addition to the eleven CRW BBMV-specific lines, four lines with cross-reactivity to ECB BBMVs were isolated. The fifteen lines represent monoclonal lines secreting IgG1, Ig2a, IgG2b, IgG3 and IgM. Monoclonal lines were analyzed by western blot to confirm CRW specificity and absence of cross-reactivity to either rabbit or corn microsomes. The specific binding of the antibodies to various CRW BBMV proteins was also characterized and shown in FIG. 1. Five distinct binding patterns were found; two patterns were specific for one or two proteins and the other three represent binding to 7–15 proteins. The class with 7–15 proteins was further subclassed into A, B, C based on binding pattern.

Western Analysis of Monoclonal Lines:

Brush border membrane vesicles were prepared as described above and electrophoresed on 8–16% acrylamide SDS protein gels (Novex, San Diego, Calif.). Proteins were transferred onto nitrocellulose, (Burnette, W. N., Western Blotting, 112:195 (1981)) and allowed to bind the supernatant of hybridoma lines. Binding of antibodies to blotted proteins was visualized using standard methods (see, for example, Antibodies: A Laboratory Manual, E. Harlow and D. Lane, Cold Spring Harbor, 1988, and references cited therein).

Example 4: Cloning CRW Binding Antibody Domains

Various methods are known for obtaining corn rootworm specific antibody genes. One method is to clone a random library of antibody genes in a phage and screen the library for ability to bind to corn rootworm gut (CRW) proteins. Another available approach is to generate monoclonal antibodies which bind to CRW gut proteins and then clone the antibody genes from such lines. For the present example, the second method is used. Antibody genes can be cloned from hybridoma cells using primers to conserved DNA sequences within the constant regions and the framework regions of the variable regions and amplified for cloning using the polymerase chain reaction (PCR). See generally, Mullis et al., Meth. Enzymol., 155:335–350 (1987); Erlich, (ed.), PCR Technology, Stockton Press (New York 1989). A database of mouse heavy chain and light chain sequences compiled by Kabat et al., U.S. Dept Health and Human Services, U.S. Government Printing Offices (1987) has been successfully used to generate both isotype specific and degenerate primers for cloning antibody genes. (Jones et al. Bio/technology 9:88–89 (1991)). Additionally, techniques are well known for cloning of smaller fragments of antibodies (Fab) which possess the binding properties of the original antibody. Complete antibodies are large molecules (150 kDa), but much smaller Fab and Fv antigen-binding fragments (12 kDa–50 kDa) have been shown to retain full binding affinity. Single chain Fv fragments (scFv) in which Vh and Vl domains are linked by a hydrophilic and flexible peptide have been used successfully to target enzymes and toxins to specific cells (Bird, Science 423:423–426 (1988); Huston, PNAS 85:5879–5883 (1988)). Single Vh domains (Dabs) and single complementary determining regions as small as 20 amino acids in length, called minimal recognition units (m.r.u.), have also been used for antigen binding (Ward, Nature 341:544–546 (1989); Taub, J. Biol. Chem 264:259–265 (1989); Williams, PNAS 86:5537–5541 (1989)). Thus, it is possible to reduce the CRW specific binding domain to a very small size.

Cloning Antibody Genes by PCR:

Polymerase chain reaction technology and specific oligonucleotide primers were used to clone immunoglobulin genes or regions from immunoglobin genes. PCR primers specific for both the heavy and light chains of IgM and the three IgG isotypes were selected from the Kabat database described above. Primers for the region encoding the NH2-terminal end of the mature variable region were designed to initiate at the first framework region and were made with some degeneracy to allow these to be used as "universal primers". The 3' primers used for the specific PCR amplification of the variable regions were designed from conserved sequences of the fast constant domain (CH1) of both the light and heavy chains. A different 3' primer was used for immunoglobulin isotypes IgG1 (3B1 and 17F6), IgG3 (10B6), and IgM (2B5). Isotypes IgG2A and IgG2B can be amplified with the same primers used for IgG 1. Antibody variable regions were cloned into a light (pCIB4612) and heavy (pCIB4611) chain expression vector containing an endoplasmic reticulum signal peptide and the constant regions of IgG1 light and heavy chains, respectively.

Table 2 shows the structure of the primers used for the PCR cloning of the mouse immunoglobulin light and heavy variable regions. Alternatively, primer sequences can be used that are available in the published literature (Coloma et al. Bio/Techniques 11: 152–156, 1991; Jones et al. Bio/ Technology 9:88–89, 1991). Oligonucleotides were made on an Applied Biosystems DNA synthesizer 380B (Applied Biosystems, Foster City, Calif.) using standard conditions as described below. The PCR primers incorporate restriction sites and, after amplification and digestion, were cloned into a plant expression vector under the control of the CaMV 35S promoter. Restriction sites were chosen that were known to be absent in sequenced antibody genes.

TABLE 2

| PCR PRIMERS USED FOR AMPLIFICATION OF ANTIBODY GENES |
|---|
| 3B1, 2B5, 10B6, 14G1 and 17F6 Light Chain Variable Regions in pCIB4614, pCIB4616, pCIB4625, pCIB4636 and pCIB4617: |
| NC92: 5' Primer    5'-GTC TCG AGG AYA TYS WGM TSA CCC ART CT-3' (SEQ ID NO: 37) |
| NC130: 3' Primer    5'-GCA GAT CTA GTT GGT GCA GCA TCA GCC CG-3' (SEQ ID NO: 38) |
| 3B1 and 17F6 Heavy Chain Variable Region in pCIB4613 and pCIB4609: |
| NC91: 5' Primer    5'-GTC TCG AGC AGG TSM ARC TGC AGS AGT CWG-3' (SEQ ID NO: 39) |
| NC114: 3' Primer    5'-GCA GAT CTA GAT CCA GGG GCC AGT GGA TA-3' (SEQ ID NO: 40) |
| 2B5 Heavy Chain Variable Region in pCIB4615: |
| NC91: 5' Primer    5'-GTC TCG AGC AGG TSM ARC TGC AGS AGT CWG-3' (SEQ ID NO: 39) |
| NC111: 3' Primer    5'-GCA GAT CTG CAG GAG ACG AGG GGG AAG ACA TT-3' (SEQ ID NO: 41) |

TABLE 2-continued

PCR PRIMERS USED FOR AMPLIFICATION OF ANTIBODY GENES

10B6 Heavy Chain Variable Region in pCIB4637:

DB91: 5' Primer  5'-ACG TCT CGA GGA RGT GAA GCT KRW KGA RWC TG-3'
(SEQ ID NO: 48)
NC117: 3' Primer  5'-GCA GAT CTG CAG CCA GGG ACC AAG GGA TA-3'
(SEQ ID NO: 42)

14G1 Heavy Chain Variable Region in pCIB4635:

DB91: 5' Primer  5'-ACG TCT CGA GGA RGT GAA GCT KRW KGA RWC TG-3'
(SEQ ID NO: 48)
DB114: 3' Primer  5'-CAA TTC GCA TAT GAG ATC CAG GGG CCA GTG GAT A-3'
(SEQ ID NO: 49)

Y = C or T;
S = C or G;
W = A or T;
M = C or A;
R = A or G

Poly-A+ RNA isolated from hybridoma lines was used to generate first swand cDNA for subsequent use in PCR reactions. Poly-A+ RNA was extracted from $10^8$ hybridoma cells using a procedure based on guanidinium thiocyanate lysis and oligo (dT) cellulose purification using the Fast Track mRNA Isolation Kit. (Invitrogen Corp., San Diego, Calif.). Approximately one tenth of the RNA isolated from $10^8$ cells (or ~500 ng) was used to generate first strand cDNA. RNA was incubated at 42° C. for 30 min then heated to 95° C. for 5 min with a mixture of deoxynucleotides (0.2 mM each dNTP), 5 µg random hexamer pd (N6) (Pharmacia LKB Biotechnology Inc., Piscataway, N.J.) as primer, 50 units Moloney Murine Leukemia Virus reverse transcriptase (Pharmacia LKB Biotechnology Inc., Piscataway, N.J.) and 1X PCR buffer in a 100 µl reaction volume. The first-strand cDNA reaction was extracted with phenol-chloroform and centrifuged through a size exclusion spin column (Chroma Spin 30, Clontech Laboratories, Inc., Palo Alto, Calif.) to remove random hexamers. Next, one tenth (or 10 µl) of the first-strand cDNA reaction was added to a 50 µl PCR reaction mix containing immunoglobulin specific primers following the instructions of the Perkin-Elmer Cetus Amplification Kit. The mixture was amplified using the Perkin-Elmer Cetus Thermal Cycler for 20 cycles. The temperature and times used for PCR were as follows: denaturation at 94° C. for 1 min; annealing at 52° C. for 1 min 30 sec; extension at 72° C. for 1 min. PCR products were electrophoresed on 6% acrylamide gels (Novex, Encinitas, Calif.) and DNA purified from gel slices. Gel slices were crushed in 200 µl TE and purified by centrifugation through Ultrafree-MC Millipore columns (Millipore, Bedford, Mass.). Eluate was treated with 50 µg/ml proteinase K at 37° C. for 30 min, extracted with phenol-chloroform-isoamyl (50:48:2), followed by an additional chloroform extraction and ethanol precipitated. DNA was resuspended in 40 µl TE and digested with appropriate restriction enzymes. PCR products of antibody variable regions were digested with Xho I and Bgl II and re-purified on 6% acrylamide gels as described above. Final Xho I/Bgl II fragments were ligated to either the light (pCIB4612) or the heavy (pCIB4611) antibody chain expression vector digested with Xho I and Bgl II. Expression vector pCIB4612 contains the CaMV 35S promoter and termination sequence with a 19 amino acid signal peptide sequence and the light chain constant region CH1. Variable light chain regions were cloned into the Xho I/Bgl II site for expression of a full length light chain.

All antibody genes were cloned by the above procedure except the heavy chain of 10B6 and the heavy and light chains of 14G1. These antibody genes were cloned from PCR products, but the products were separated by electrophoresis on 6% acrylamide THE gels, the fragments cut out of the gel and eluted into 0.7M LiCl plus 2 mM EDTA. The fragments were precipitated and resuspended in 10 mM Tris plus 2 mM EDTA, pH 7.5. The isolated PCR products were ligated directly into a pUC derived cloning vector, pT&Blue T (Novagen, Inc.). Since Taq DNA polymerase leaves a single 3' A-nucleotide overhang on the reaction products (Clark, Nucl. Acids Res. 16:9677 (1988)), these products can be cloned directly into a vector containing compatible single T-nucleotide overhangs (Marchuk et al. Nucl. Acids Res. 19:1154 (1990)).

The pCIB4612 vector was made by ligating a 155 base pair Dde I/Sty I light chain constant region from a mouse Ig Kappa chain (Schulze-Gahmen et al. 1988, J. Biol. Chem. 263:1700–1706; Kabat et al., U.S. Dept Health and Human Services, U.S. Government Printing Offices (1987)) in a four way ligation to a 71 bp Xho I/Dde I fragment, a 101 bp Sty I/Bgl II fragment, and a 3.8 Kb Xho I/Bgl II vector fragment from pCIB4610. Oligonucleotides KE109A28 and KE110A28 were hybridized to make the 101 bp fragment with StyI and Bam HI staggered ends.

KE109A28: 5'-CAA GGA CGA GTA TGA ACG ACA TAA CAG CTA TAC
CTG TGA GGC CAC TCA CAA GAC ATC AAC TTC ACC CAT TGT CAA
GAG CTT CAA CAG GAA TGA GTG TTA GG-3' (SEQ ID NO:19)

KE110A28: 5'-GAT CCC TAA CAC TCA TTC CTG TTG AAG CTC TTG
ACA ATG GGT GAA GTT GAT GTC TTG TGA GTG GCC TCA CAG GTA
TAG CTG TTA TGT CGT TCA TAC TCG TC-3' (SEQ ID NO:20)

Oligonucleotides KE111A28 and KE112A28 were hybridized to make the 71 bp fragment with Xho I and Dde I staggered ends.

KE111A28: 5'-TCG AGG GTA CCG AGC TCT AGA TCT GTA TCC ATC
TTC CCA CCA TCC AGT GAG CAG TTA ACA TCT GGA GGT GCC-3' (SEQ ID NO:21)

KE112A28: 5'-TGA GGC ACC TCC AGA TGT TAA CTG CTC ACT GGA
TGG TGG GAA GAT GGA TAC AGA TCT AGA GCT CGG TAC CC-3' (SEQ ID NO:22)

Expression vector pCIB4611 contains heavy chain constant regions CH1–CH3, and likewise variable heavy chain regions can be cloned into the Xho I/Bgl I1 site for expression of a full length heavy chain. The pCIB4611 vector was made by ligating a Nco I/Bst XI 902 bp heavy chain constant region from a mouse IgGG1 Gamma chain (Honjo, et al. 1979, Nature 277:627–633; Kabat et al., U.S. Dept Health and Human Services, U.S. Government Printing Offices (1987)) with two 40 bp hybridized oligonucleotide fragments and ligating the final 982 bp fragment into pCIB4610 digested with Bgl II and Xho I. One 40 bp fragment was hybridized from oligos KE106A28 and KE107A28 and has Xho I/Nco I staggered ends and the other 40 bp fragment was hybridized from KE108A28 and KE105A28 and has Bst XI/Bam HI staggered ends.

pCIB4615: 2B5 heavy chain variable region (NRRL B-21216)
pCIB4616: 2B5 light chain variable region (NRRL B-21217)
pCIB4609: 17F6 heavy chain variable region (NRRL B-21215)
pCIB4617: 17F6 light chain variable region (NRRL B-21218)
pCIB4637: 10B6 heavy chain variable region (NRRL B-)
pCIB4625: 10B6 light chain variable region (NRRL B-21219)
pCIB4635: 14G1 heavy chain variable region (NRRL B-21277)
pCIB4636: 14G1 light chain variable region (NRRL B-21278)

KE106A28: 5'-TCG AGG GTA CCG AGC TCT AGA TCT GCT GCC CAA ACT AAC TC-3' (SEQ ID NO:23)
KE107A28: 5'-CAT GGA CTT AGT TTG GGC AGC AGA TCT AGA GCT CGG TAC CC-3' (SEQ ID NO:24)
KE108A28: 5'-CTG GTA AAG GCG GCC GCA TCG ATT AAG TCG ACC CGC GGG-3' (SEQ ID NO:25)
KE105A28: 5'-GAT CCC CGC GGG TCG ACT TAA TCG ATG CGG CCG CCT TTA CCA GGA GA-3' (SEQ ID NO: 26)

The pCIB4610 vector contains a 19 amino acid mouse endoplasmic reticulum signal peptide sequence between CaMV 35S promoter and CaMV 35S termination sequences. The pCIB4610 vector was made by ligating pCIB4600 digested with Bam HI and Hpa I to a 83 bp PCR generated fragment digested with Bam HI and Hpa I. The PCR generated fragment was made using pCIB4600 as a template and PCR primers KE102A28 and KE101A28. PCIB4610 differs from pCIB4600 only in the untranslated leader region following the CaMV 35S promoter. pCIB4610 contains a plant consensus translational initiation sequence AACA ATG (SEQ ID NO:27) where ATG is the start of translation, and pCIB4600 contains the sequence TCCG ATG (SEQ ID NO:28).

The expression vectors listed above that are followed by an NRRL accession number were deposited on Mar. 7, 1994 with Agricultural Research Service, Patent Culture Collection (NRRL), Northern Regional Research Center, 1815 North University Street, Peoria, Ill. 61604, U.S.A., with the exception of pCIB4637, pCIB4635 and pCIB4636, which were deposited on Jun. 3, 1994

Table 3 contains a listing of the sequence ID numbers for the variable region sequences. The sequence in the cases of pCIB4613, pCIB4617, pCIB4625, pCIB4637, pCIB4635 and pCIB4636 are complete variable regions starting at the fast codon of the first framework region and ending with the last codon of the fourth framework region of the variable region. The variable region in pCIB4609 is not complete, the KE102A28: 5'-CGA AGT TAA CAG ATC TAG AGC TCG G-3' (SEQ ID NO:29)
KE101A28: 5'-CGG GAT CCA ACA ATG GGA TGG AGC TGG ATC TT-3' (SEQ ID NO:30)

The pCIB4600 vector was made by ligating a derivative of the CaMV 35S expression vector pCIB710 (Rothstein, et al. (1987) Gene 53:153–161) digested with Bam HI and Sac I with a 86 bp Bam HI and Sac I fragment encoding an endoplasmic reticulum signal peptide (Kabat et al., U.S. Dept Health and Human Services, U.S. Government Printing Offices (1987)). The 86 bp fragment contains the following sequence:

5' end of the coding sequence is truncated and the sequence begins in the second CDR region of the variable region.

5'-GAT CCA ACA ATG GGA TGG AGC TGG ATC TTT CTC TTC CTC CTG
TCA GTT GTT ACC CTA CCT CGA CCT AGA AAG AGA AGG AGG ACA
GTG GAG CTG CAG GTG TCC ATT GCC TAC TCG AGG GTA CCG AGC
TCC TCG ACG TCC ACA GGT AAC GGA TGA GCT CCG ATG GC-3' (SEQ ID NO:31)

Variable light and heavy chain regions were cloned from five CRW monoclonal lines into the expression vectors to generate the following constructs:

pCIB4613: 3B1 heavy chain variable region
pCIB4614: 3B1 light chain variable region

TABLE 3

LIST OF ANTIBODY CHAIN DNA SEQUENCES

| SEQ ID NO: 1  | 3B1 Heavy chain variable region DNA     |
|---------------|------------------------------------------|
| SEQ ID NO: 2  | 3B1 Heavy chain variable region protein |
| SEQ ID NO: 3  | 3B1 Light chain variable region DNA     |
| SEQ ID NO: 4  | 3B1 Light chain variable region protein |
| SEQ ID NO: 5  | 2B5 Heavy chain variable region DNA     |
| SEQ ID NO: 6  | 2B5 Heavy chain variable region protein |
| SEQ ID NO: 7  | 2B5 Light chain variable region DNA     |
| SEQ ID NO: 8  | 2B5 Light chain variable region protein |
| SEQ ID NO: 9  | 17F6 Heavy chain variable region DNA    |
| SEQ ID NO: 10 | 17F6 Heavy chain variable region protein|
| SEQ ID NO: 11 | 17F6 Light chain variable region DNA    |
| SEQ ID NO: 12 | 17F6 Light chain variable region protein|
| SEQ ID NO: 13 | 10B6 Heavy chain variable region DNA    |
| SEQ ID NO: 14 | 10B6 Heavy chain variable region protein|
| SEQ ID NO: 15 | 10B6 Light chain variable region DNA    |
| SEQ ID NO: 16 | 10B6 Light chain variable region protein|
| SEQ ID NO: 17 | 3B1 single chain antibody DNA           |
| SEQ ID NO: 18 | 3B1 single chain antibody protein       |
| SEQ ID NO: 44 | 14G1 Heavy chain variable region DNA    |
| SEQ ID NO: 45 | 14G1 Heavy chain variable region protein|
| SEQ ID NO: 46 | 14G1 Light chain variable region DNA    |
| SEQ ID NO: 47 | 14G1 Light chain variable region protein|

Synthesis of DNA Oligomers:

DNA oligomers were synthesized using an Applied Biosystems model 380B DNA synthesizer and standard procedures. The oligomers were made using the updated SSCAF3 cycle on a 0.2 µmole, wide pore, small scale ABI column. The end procedure was run trityl off and the oligomer was cleaved from the column using the 380B's automatic cleavage cycle. The oligomers were then deblocked in excess ammonium hydroxide ($NH_4OH$) at 55° C. for 8–12 hours. The oligomers were then dried in an evaporator using nitrogen gas. After completion, the oligomers were resuspended in 0.25–0.5 ml of deionized water.

Purification of Synthetic DNA Oligomers:

An aliquot of each oligomer was mixed with an equal volume of blue dye/formamide mix with the final solution containing 0.05% bromophenol blue, 0.05% xylene cyanol FF, and 25% formamide. This mixture was heated at 95° C. for 10 minutes to denature the oligomers. Samples were then applied to a 12% polyacrylamide-urea gel containing 7M urea (Sambrook et al.). After electrophoresis at 300–400 volts for 3–4 hours using a Vertical Slab Gel Unit (Hoefer Scientific Instruments, San Francisco, Calif.), UV shadowing was used to locate the correct sized fragment in the gel which was then excised using a razor blade. The purified gel fragment was minced and incubated in 0.4M LiCl, 1 mM EDTA (pH 8) buffer overnight at 37° C.

Either of two methods was then used to separate the oligomers from the polyacrylamide gel remnants: Gene/X 25 micron porous polyethylene filter units or Millipores ultrafree-MC 0.45 micron filter units. The purified oligomers were ethanol precipitated, recovered by centrifuging in a microfuge for 20 min at 4° C., and finally resuspended in TE (10 mM Tris, 1 mM EDTA, pH 8.0). Concentrations were adjusted to 50 ng/µl based on absorption readings at 260 nm.

Kinasing Oligomers:

In each 20 µl kinase reaction, one picomole of pitied oligomer was used in a buffer of 7.0 mM Tris pH 7.5, 10 mM KCl, 1 mM $MgCl_2$, 0.5 mM DTT, 50 µg/ml BSA, 3000 µCi (3 picomoles) of $^{32}P$-γ-ATP, and 8 units of T4 polynucleotide kinase. The kinase reaction was incubated for 1 hour at 37° C., followed by a phenol/chloroform extraction and three ethanol precipitations with glycogen as carrier (Tracy, Prep. Biochem. 11:251–268 (1981)).

Hybridizing Oligomers for Direct Cloning:

Oligomers to be hybridized were pooled together (from 1 µg to 20 µg total DNA) and kinased at 37° C. for 1 hour in 1X Promega ligation buffer containing 30 mM Tris-HCl pH 7.8, 10 mM $MgCl_2$, 10 mM DTT, and 1 mM dATP. One to 20 units of T4 polynucleotide kinase was used in the reaction, depending on the amount of total DNA present. The kinasing reactions were stopped by placing the reaction in a boiling water bath for five minutes. The pooled oligomers were in a volume of 50–100 µl with added hybridization buffer used to adjust the final salt conditions to 100 mM NaCl, 120 mM Tris pH 7.5, and 10 mM $MgCl_2$. The kinased and non-kinased oligomers were pooled together and heated in a boiling water bath for five minutes and allowed to slowly cool to room temperature over a period of about four hours. The hybridized oligomers were then phenol/chloroform extracted, ethanol precipitated, and resuspended in 17•1 of TE (10 mM Tris, 1 mM EDTA, pH 8.0). Using this 17•1, a ligation reaction with a final volume of 20•1 is assembled (final conditions=30 mM Tris-HCl pH 7.8, 10 mM $MgCl_2$, 10 mM DTT, 1 mM ATP, and 3 units of T4 DNA ligase (Promega, Madison Wis.). The ligation was allowed to incubate for about 2 hours at room temperature. The hybridized/ligated fragments were generally purified on 2% Nusieve gels before and/or after cutting with restriction enzymes and prior to cloning into vectors. A 20•1 volume ligation reaction is assembled using 100 ng to 500 ng of each fragment with approximate equimolar amounts of DNA in 30 mM Tris-HCl pH 7.8, 10 mM $MgCl_2$, 10 mM DTT, 1 mM ATP, and 3 units of T4 DNA ligase (Promega; Madison, Wis.). Ligations were incubated at room temperature for 2 hours. After ligation, DNA was transformed into frozen competent E. coli cells using standard procedures (Sambrook et al.) and transformants were selected on LB-agar (Sambrook et al.) containing 100 µg/ml ampicillin (see below).

Example 5: Construction of a Single Chain Antibody (SCA) Molecule pCIB4631 contains a single chain antibody (SCA) specific to CRW BBMVs fused to the constant regions of the antibody heavy chain gene. The SCA gene contains the fusion of variable fragments from antibody 3B1 light and heavy chains, (from monoclonal antibody line 3B1 specific to CRW BBMV) with a 19 amino acid endoplasmic reticulum signal sequence. Between the light and heavy Fv fragments is a 10 amino acid (GGGGSGGGGS; SEQ ID NO:32) domain linker (Huston et al., (1988) PNAS). pCIB4631 was made by ligating a 4.1 Kb Xba I/Xho I fragment (Fv: constant heavy chain: CaMV 35S termination region: vector fragment from pCIB4613) and a 1.4 Kb Xba I/Bgl II fragment (CaMV 35S promoter: light Fv fragment from pCIB4614), and a hybridized 36 base pair linker fragment with Bgl II / Xho I staggered restriction enzyme site ends.

Oligos KE147A28 and KE182A28 were hybridized together in making a 36 base pair linker.

KE147A28: 5'-GAT CTG GTG GCG GTG GCT CGG GCG GTG GTG GGT CCA-3' (SEQ ID NO: 33)

KE182A28: 5'-TGC AGC GAC CCA CCA CCG CCC GAG CCA CCG CCA CCA-3' (SEQ ID NO:34)

Oligomers were purified as described above on a 12% polyacrylamide/7M urea gel using UV shadowing to cut-out the correct size oligomers using standard procedures. Oligos were kinased and hybridized as described above.

Expression vector pCIB4631 was deposited on Mar. 7, 1994 with the Agricultural Research Service, Patent Culture Collection (NRRL), Northern Regional Research Center, 1815 North University Street, Peoria, Ill. 61604, U.S.A. and was assigned accession number NRRL B-21220.

Example 6: Characterization of SCA Binding Properties.

Single chain antibody proteins were expressed in maize protoplasts, isolated, and shown to bind CRW BBMV proteins on both a western blot and isolated cross-sections of CRW midguts in immunosections (Bravo et al. 1992, J. of Invert. Path. 60:237–246, Bravo et al. 1992, J. of Invert. Path. 60:247–253).

Isolation of Maize Suspension Cell Protoplasts:

Embryogenic suspension cultures derived from immature embryo cultures of a Ciba Seeds maize inbred (B73 type) were maintained in N6 basal medium (Chu et al., 1975) supplemented with 3% sucrose and 2 mg/l 2, 4-D, at 27° C. on a gyratory shaker at 130 rpm and sub-cultured weekly. Suspension cells were collected 1–2 days after subculturing and resuspended in enzyme solution (3% cellulase RS+1% macerozyme R10 dissolved in KMC: 8.7 g/l KCl, 12.5 g/l $CaCl_2$, 16.4 g/l $MgSO_4$, 5 g/l MES, pH 5.7) at a ratio of 2 ml packed cell volume per 20 ml enzyme solution. Cells were aliquoted into 100×25 mm Petri dishes and incubated for four hours at room temperature on a gyratory shaker at 50 rpm.

Transformation of Protoplasts:

Immediately after isolation, protoplasts were resuspended at a density of 6 million/ml in RS buffer (0.45M mannitol, 15 mM $CaCl_2$, 0.1% MES, pH 5.7). One-half ml aliquots were placed in 17×100 mm polystyrene tubes, followed by 50 μg pCIB4631 DNA and 50 μg CaMV 35S GUS or luciferase plasmid DNA (as transformation control). One-half ml of PEG solution (40% PEG 6000, 0.4M mannitol, 0.1M $Ca(NO_3)_2$ was added to each tube and mixed with protoplasts by gentle shaking. After a 30 min incubation at room temperature, protoplasts were diluted stepwise at 5 minute intervals with 1 ml, 2 ml, 5 ml, and 10 ml W5 (9.0 g/l NaCl, 18.5 g/l $CaCl_2$, 0.37 g/l KCl, 0.9 g/l glucose pH 5.6), sedimented, and resuspended in plating medium (MS salts, B5 vitamins, 3% sucrose, 2 mg/l 2,4-D, 0.3M mannitol) at a density of $2 \times 10^6$ protoplasts/ml. Protoplasts were incubated in the dark at 26° C. At 18–22 hrs, protoplasts were collected in Eppendorf tubes, sedimented, and resuspended in 0.4 ml extraction buffer (100 mM $KHPO_4$ pH 7.8, 1 mM DTT). Samples were then sonicated for 10 seconds and debris pelleted by centrifugation.

Single Chain Antibody Binding to CRW BBMV:

Brush border membrane vesicles were prepared as described above and electrophoresed on 8–16% acrylamide SDS protein gels (Novex, San Diego, Calif.). Proteins were transferred onto nitrocellulose (Burnette, W. N., Western Blotting, 112:195 (1981) and allowed to bind maize protoplast extracts containing the single chain antibody protein. The CRW BBMV-specific 3B1 single chain antibody protein expressed from pCIB4631 bound the same molecular weight BBMV protein on the western blot as did the original 3B1 monoclonal. The single chain antibody expressed in maize protoplasts was also shown to bind to cross-sections of CRW midgut in immunosectioning experiments (Bravo et al. 1992, J. Invert. Path. 60:237–246, Bravo et al. 1992, J. Invert. Path. 60:247–253).

Example 7: Construction of CRW Specific Immunotoxin

A CRW BBMV specific single chain antibody was fused to the toxic domain from Pseudomonas exotoxin A. Pseudomonas exotoxin A has been used to synthesize recombinant hybrid antibody-toxin fusion proteins for treatment of cancer and immunological diseases (Pastan, L and FitzGerald, D., 1989, J. Biol. Chem. 264:15157–15160, and Pastan, I et al. Annu. Rev. Biochem. 1992 61:331–54). The structure of Pseudomonas exotoxin is well characterized and its mode of action known. The idea of antibody hybrid toxins as insecticidal agents is novel and there is no precedent for this type of approach.

Pseuodomonas exotoxin (PE) is a single chain toxin secreted by *Pseudomonas aeruginosa*. It kills cells by catalyzing the irreversible ADP-ribosylation and inactivation of translational elongation factor 2 (EF-2). The structure of PE is well characterized (Chaudhary, V. K. et al., 1990, J. Biol. Chem. 265:16303–16310), and consists of three domains. Domain Ia is responsible for the cell recognition and binding of PE to target cells, domain II is required for the translocation of the ADP-ribosylating activity into the cytosol and domain III is the ADP-ribosylating activity. When the toxin enters the cell it is internalized by endocytic vesicles where cleavage occurs to generate a 37 kD domain III "activated toxin". Deletion of domain Ia removes the cell binding domain and generates a 40 kDa protein (PE40) with "extremely low" cellular cytotoxicity. The fusion of antibodies to PE40 has been used to make many recombinant immunotoxins for cancer therapy. It is believed that the binding of the antibody-PE40 fusion must be followed by internalization by receptor-mediated endocytosis for proper activation of the PE40 and subsequent passage to the cytosol.

The PE toxic domain was fused to the —COOH terminus of the heavy chain fragment of the CRW 3B1 single chain since it has been shown that fusions to the —NH2 terminus of PE40 retain cytotoxicity. It is also possible to design the fusions such that the single-chain antibody is fused to the —COOH terminus of PE40 (Prior et al. Cell Vol. 64:1017–1023). Single-chain antibody fusions were made and tested in *E. coli* expression vectors, using the p-FLAG expression vector which has an IPTG inducible me promoter followed by sequences encoding the ompA signal peptide for secretion into the periplasm and the eight amino acid FLAG epitope which allows the isolation of recombinant protein by antibody affinity chromatography. Single chain antibody fusion proteins were purified from the FLAG expression vector. The purified SCA fusion proteins are incorporated into a corn rootworm insect diet for activity assays.

A single chain antibody fused to PE40 was made by ligating a ~1.2 Kb Sph I/Eco RI fragment containing PE40 and a 790 bp Hind III/Sph I fragment containing the 3B1 single chain antibody into the 5.37 Kb Hind III/Eco RI digested pFLAG vector (IBI, New Haven, Conn.). The PE40 fragment was obtained from pWW20, a vector containing the toxic domain of Pseudomonas exotoxin A under control of an inducible Lac promoter in a pUC9 vector (Wels et al. 1992, Cancer Research 52:6310–6317). The 700 bp fragment containing the 3B1 single chain antibody was generated by PCR using pCIB4631 as template and PCR oligos NC200 and NC202.

NC200: 5'-CGA AGC TTG ACA TTG TGC TGA CCC AG-3' (SEQ ID NO:35)

NC202: 5'-GCC CTC TAG AAG CAT GCC TGA GGA GAC GGT GAC TGA-3' (SEQ ID NO: 36)

Example 8: Transformation and Expression in Plants

Hybrid toxins comprised of antibody domains fused to toxin domains are transformed into plants using current methodology as set forth in U.S. application Ser. Nos. 07/951,715, 08/008,006, and 08/037,057. Binary toxins comprised of two independent antibody chains or antibody domains fused to toxins are expressed and assembled in plants using normal cellular processing. Single chain antibody-toxin proteins are either expressed in the plant cytoplasm, targeted to the plant apoplast, or in the case of hybrid toxins that have cellular toxicity, targeted to organelles within the plant cell (Taviadoraki et al. 1993, Nature 366:469–472; Owen et al. 1992, Bio/Technology 10: 790–794; Firek et al. 1993, Plant Molecular Biology 23: 861–870). Techniques known in the literature are used to target proteins to the chloroplast or the vacuole via the endoplasmic reticulum. Vacuolar targeting signals in the form of carboxyl-terminal propeptides are described in the literature (Bednarek S. et al. 1991, Plant Cell 3:1195–1206; Neuhaus J-M et al. 1991, PNAS 88:10362–10366;Bednarek S. et al. 1992, Plant Mol. Biol. 20:133–150, Chrispeels M. J. et al. 1992, Cell 68:613–616; Nakamura K. et al. 1993, Plant Physiol. 101:1–5; Dombrowski J. E. et al. 1993, Plant Cell 5:587–596; Schroeder M. R. et al. 1993, Plant Physiol 101:451–458). Chloroplast targeting signals in the form of N-terminal transit peptides are described in the literature (Van Den Broeck G. et al. 1985, Nature 313:358–363; Smeekens S. et al. 1987, Plant Mol. Biol. 9:377–388; Szabo L. J. et al. 1987, In *Plant DNA Infectious Agents*, eds. T. Hohn and J. Schell Springer Verlag, Wein, New York, pp. 321–339; Keegstra K. et al. 1989, Annu. Rev. Plant Physiol. Plant Mol. Biol. 40:471–501).

The present invention provides material and methods for the construction of toxin molecules which ate targeted to a particular insect. Insects which have evaded toxin binding and cytotoxic effects of Bt endotoxins are specifically targeted. Furthermore, the toxin molecules are constructed so that they are specific to the particular insect pest.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to he incorporated by reference. Although the foregoing invention has been described in some detail by way of illustration and example for purposes of clarity of understanding, it will be obvious that certain changes and modifications may be practiced within the scope of the claims.

---

What is claimed is:

1. A DNA sequence which encodes a variable region of a light chain of a monoclonal antibody which binds to the gut of a target insect but does not bind to mammalian brush border membranes or to plant microsomes, wherein said DNA sequence is selected from the group consisting of SEQ ID NOS. 3, 7, 11, 15 and 46.

2. A DNA sequence which encodes a variable region of a heavy chain of a monoclonal antibody which binds to the gut of a target insect but does not bind to mammalian brush border membranes or to plant microsomes, wherein said DNA sequence is selected from the group consisting of SEQ. ID Nos. 1, 5, 9, 13, and 44.

3. An amino acid sequence encoded by the DNA sequence of claim 1.

4. An amino acid sequence encoded by the DNA sequence of claim 2.

5. A DNA sequence which encodes a single chain antibody which binds to the gut of a target insect but does not bind to mammalian brush border membranes or to plant microsomes, wherein said DNA sequence is SEQ ID NO: 17.

6. An amino acid sequence encoded by the DNA sequence of claim 5.

* * * * *